US006464984B2

(12) United States Patent
Audonnet et al.

(10) Patent No.: US 6,464,984 B2
(45) Date of Patent: *Oct. 15, 2002

(54) AVIAN POLYNUCLEOTIDE VACCINE FORMULA

(75) Inventors: Jean-Christophe Audonnet, Lyons (FR); Annabelle Bouchardon, Lyons (FR); Michel Riviere, Ecully (FR)

(73) Assignee: Merial, Lyons (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/784,990

(22) Filed: Feb. 16, 2001

(65) Prior Publication Data

US 2002/0037292 A1 Mar. 28, 2002

Related U.S. Application Data

(60) Division of application No. 09/232,479, filed on Jan. 15, 1999, now Pat. No. 6,221,362, which is a continuation-in-part of application No. PCT/FR97/01326, filed on Jul. 16, 1997.

(51) Int. Cl.[7] ...................... A61K 39/17; A61K 39/295; A61K 39/145; A61K 15/00; C07H 21/04
(52) U.S. Cl. ................. 424/214.1; 424/199.1; 424/202.1; 424/209.1; 435/320.1; 536/23.72
(58) Field of Search ............................ 424/199.1, 206.1, 424/201.1, 204.1, 202.1, 209.1, 229.1, 214.1, 320.1; 536/23.72

(56) References Cited

U.S. PATENT DOCUMENTS 5,916,879 A 6/1999 Webster
6,221,362 B1 * 4/2001 Audonnet et al. ....... 424/199.1

FOREIGN PATENT DOCUMENTS

| WO | WO 95/20660 | 8/1995 |
|---|---|---|
| WO | WO 96/12808 | 5/1996 |
| WO | WO 96/21034 | 7/1996 |

OTHER PUBLICATIONS

Babiuk et al. Veterinary Immunology and Immunopathology. 1999; 72: 189–202.*
Webster et al., Vaccine, 1994, vol. 12 (16), pp. 1495–1498.
Robinson et al., Vaccine, 1993, vol. II (9), pp. 957–960.
Xiang et al. Immunity, 1995, vol. 2, pp. 129–135.
Xiang et al. Virology, 1995, vol. 209, pp. 569–579.
O'Meara et al., Immunology and Cell Biology, 1993, vol. 71 (pt5), pp. 473–488.
Sakaguchi et al. (1996) "Protection of chickens from Newcastle disease by vaccination with a linear plasmid DNA expressing the F protein of Newcastle disease virus" Vaccine 14:747–752.
A.J. Douglas et al., Identification of a 24kDa Protein Expressed Anaemia Virus; Journal of General Virology (1995), vol. 76, pp. 1557–1562.
B.M. Meehan et al., Characterization of Viral DNAs From Cells Infected with Chicken Anaemia Agent: Sequence Analysis of the Cloned Replicative Form and Cloned Genome Fragments; Arch Virol, (1992), vol. 124 pp. 301–319.
D. Todd et al., Investigation of the Transfection Capability of Cloned Tandemly–Repeated Chicken Anaemia Virus DNA Fragments; Arch Virol (1996) vol. 141, pp. 1523–1534.

* cited by examiner

*Primary Examiner*—James Housel
*Assistant Examiner*—Shanon Foley
(74) *Attorney, Agent, or Firm*—Frommer Lawrence & Haug LLP; William S. Frommer; Thomas J. Kowalski

(57) ABSTRACT

An avian plasmid vaccine contains a plasmid, and a pharmaceutically acceptable carrier. The plasmid contains and expresses in vivo in an avian host cell a nucleic acid molecule having a sequence encoding the Newcastle disease virus HN protein. The plasmid can further contain and express in vivo in an avian host cell a nucleic acid molecule having a sequence encoding the Newcastle disease virus F protein.

13 Claims, 28 Drawing Sheets

Figure 1:
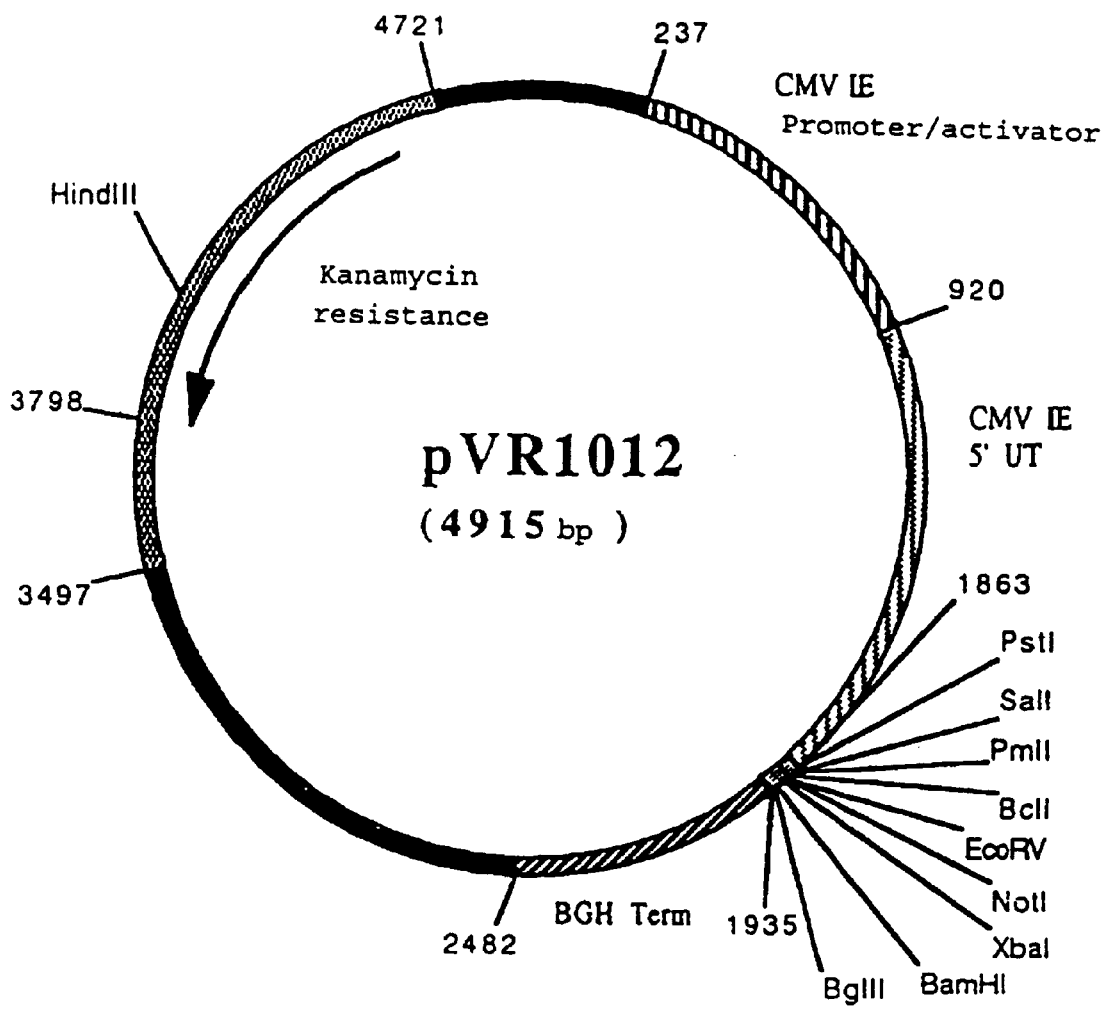
Figure 2:
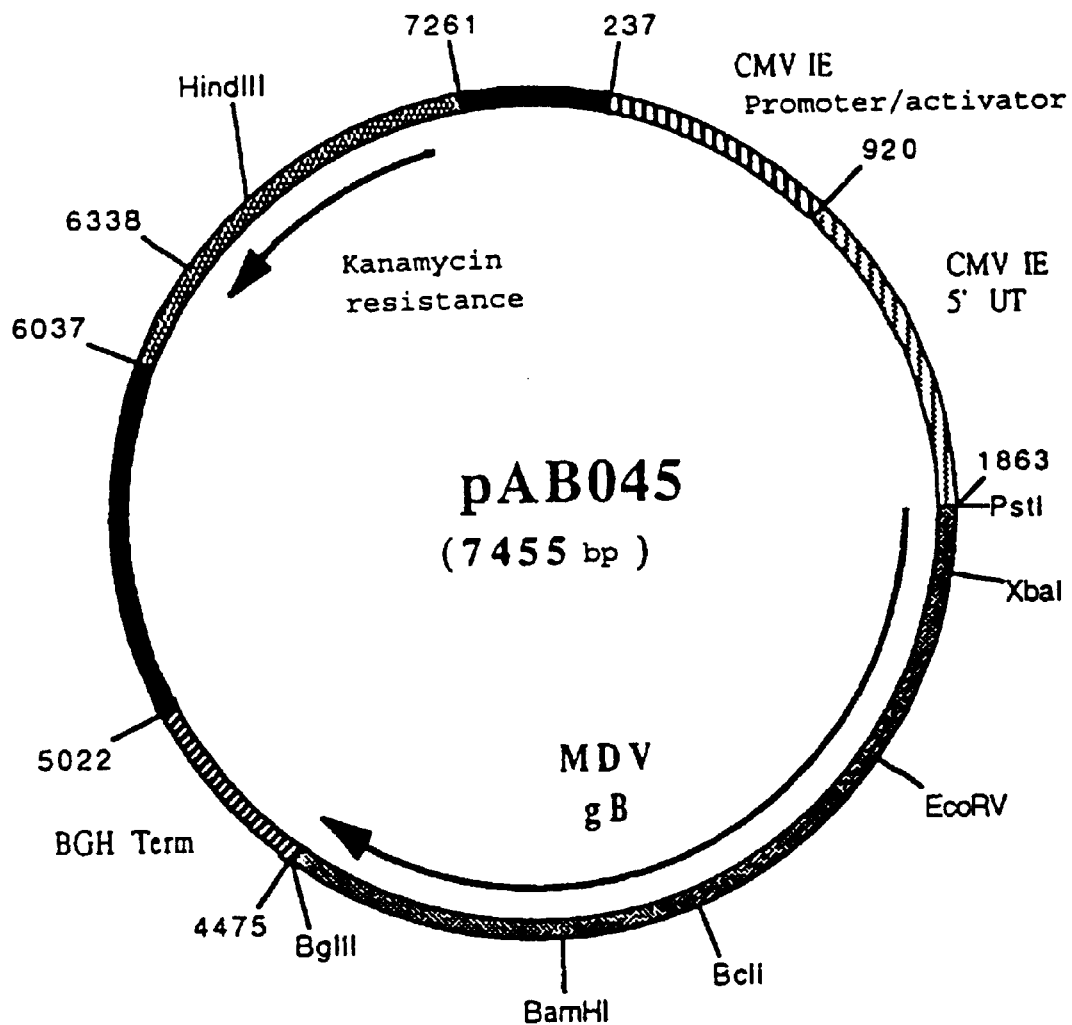
Figure 3:
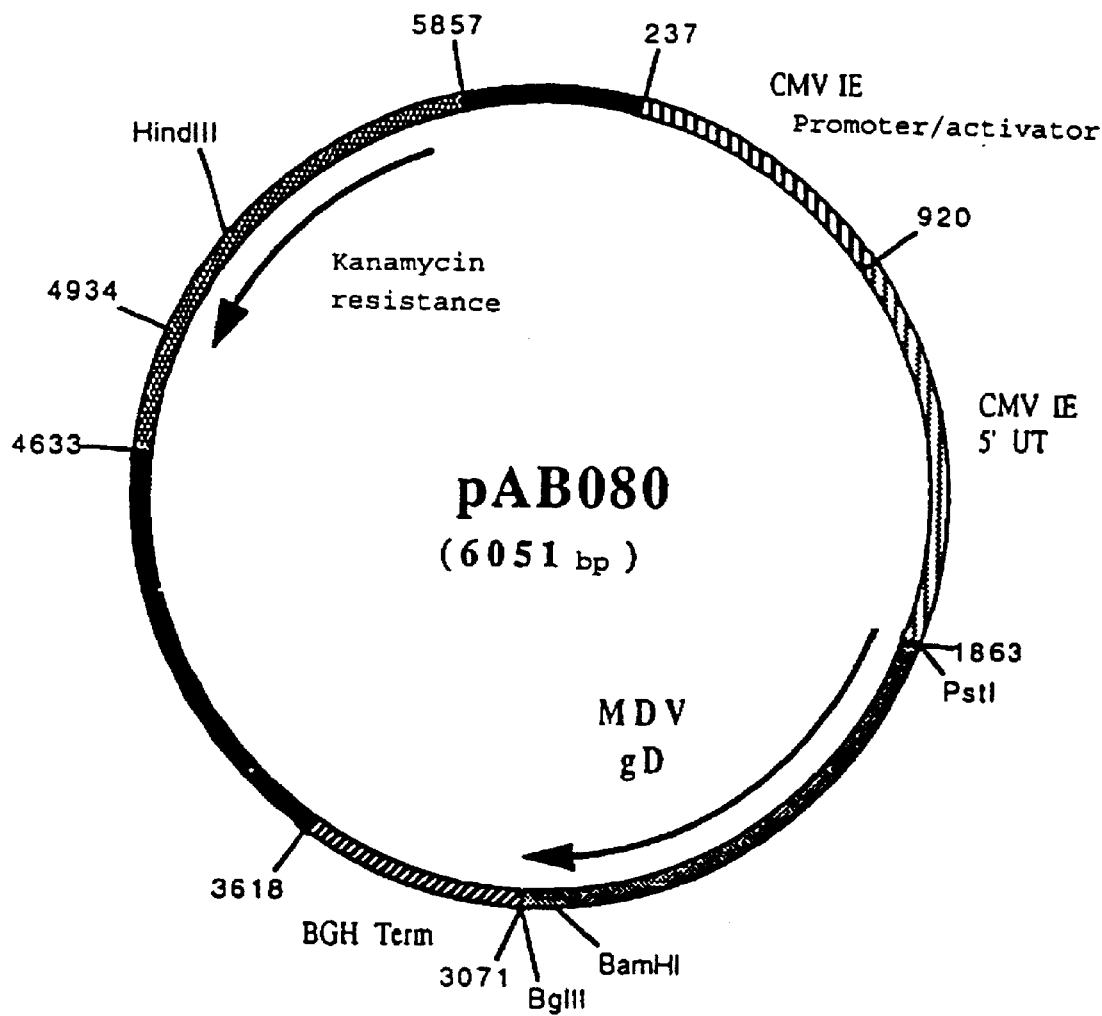
Figure 5:
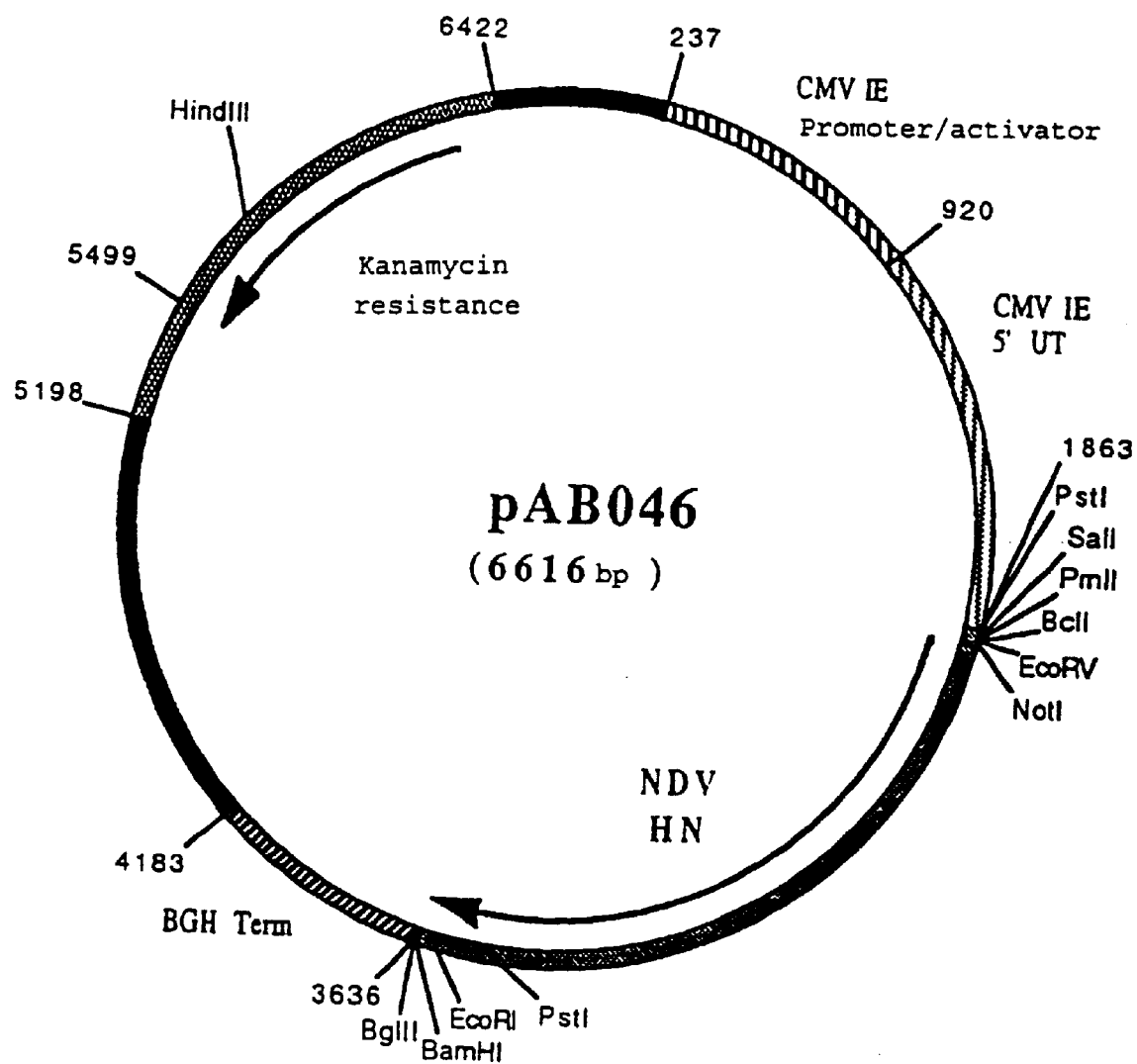
Figure 7:
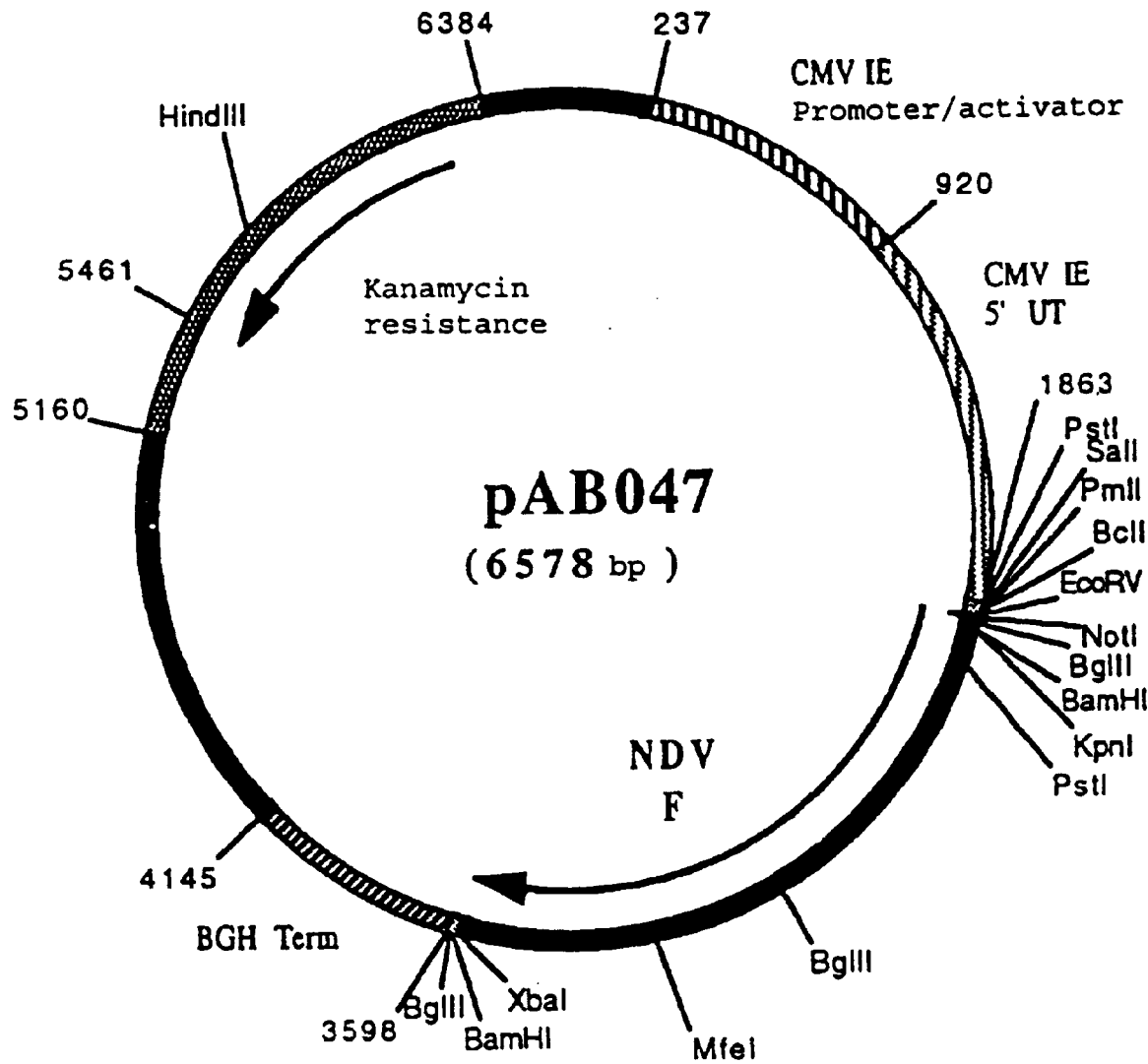
Figure 9:
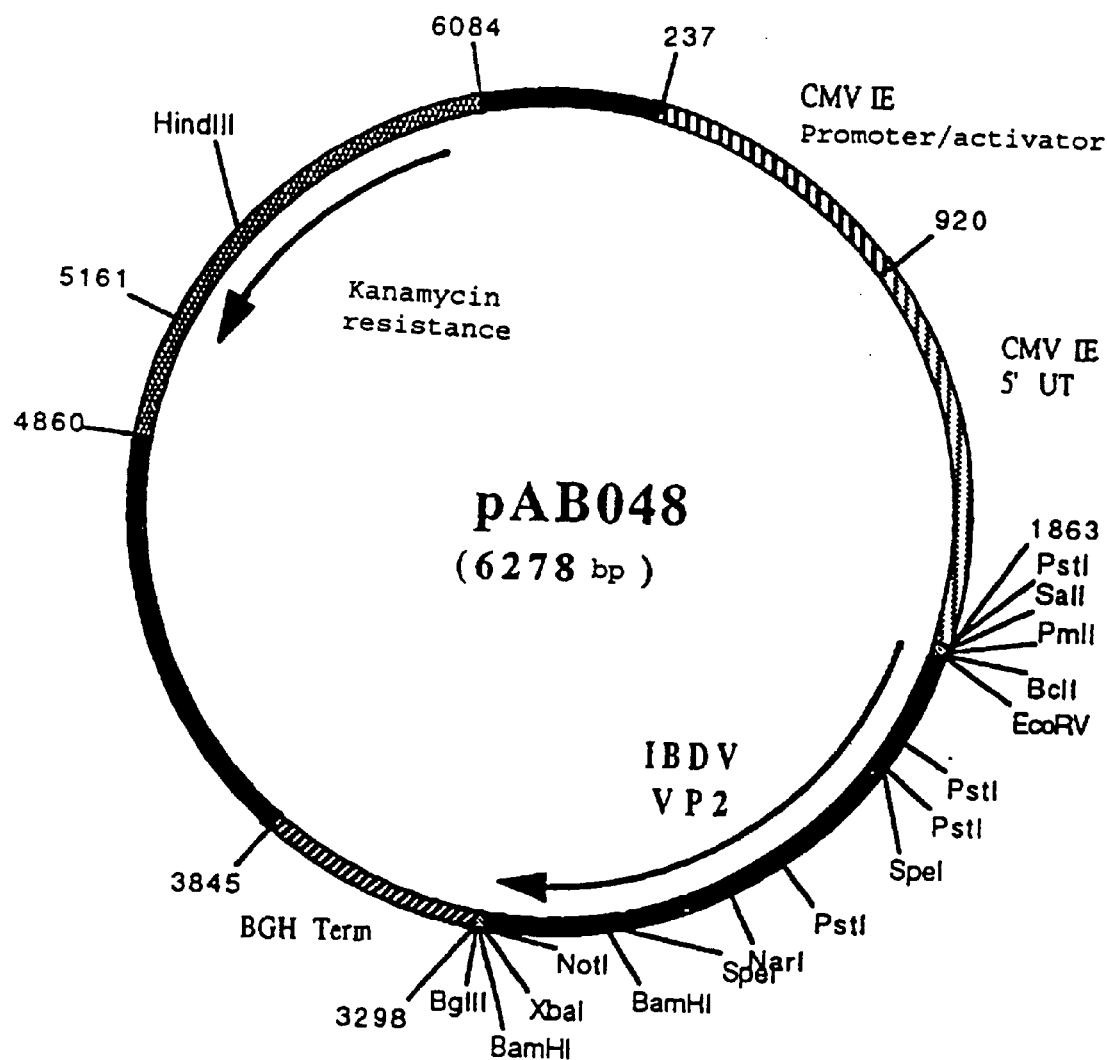
Figure 11:
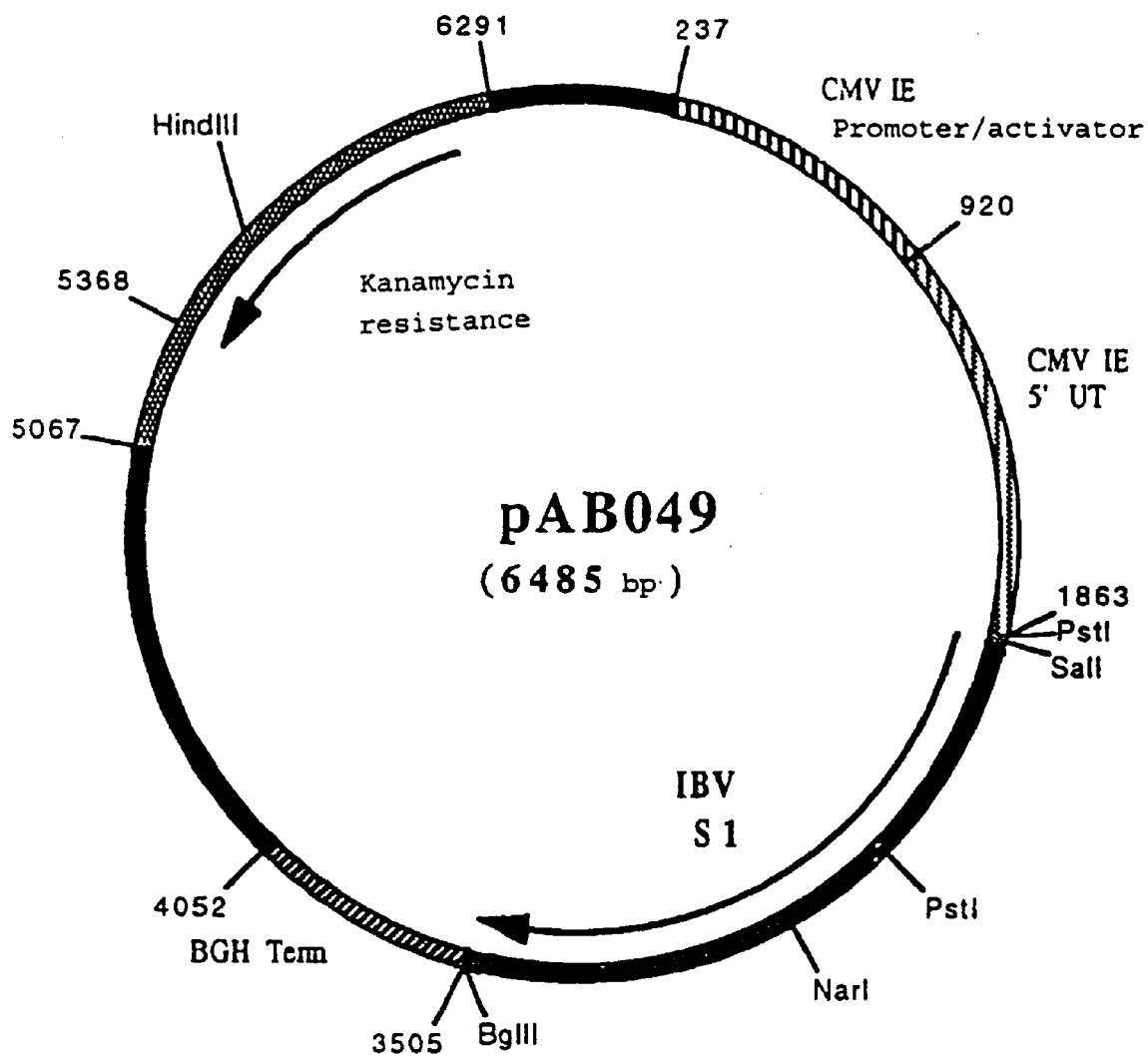
Figure 13:
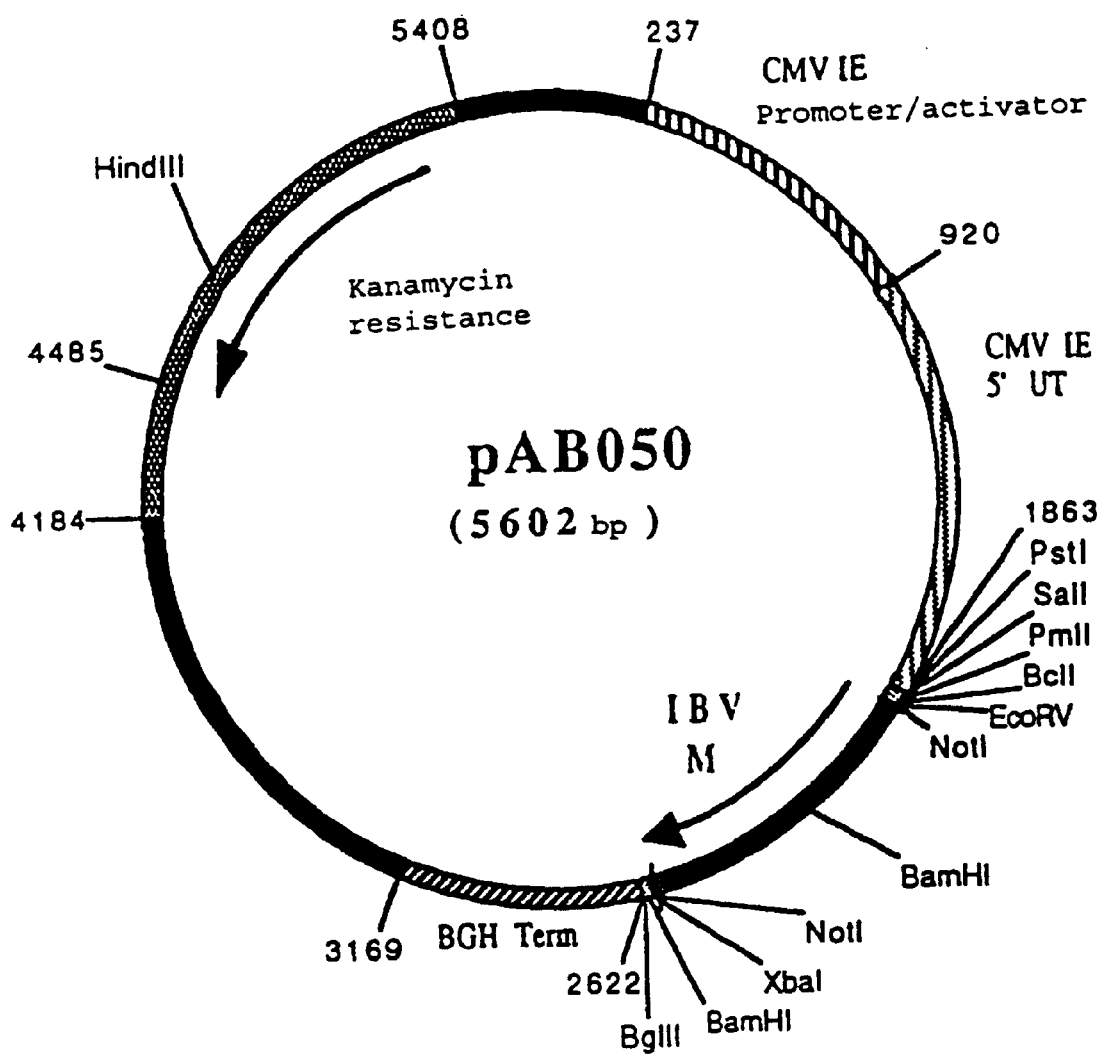
Figure 15:
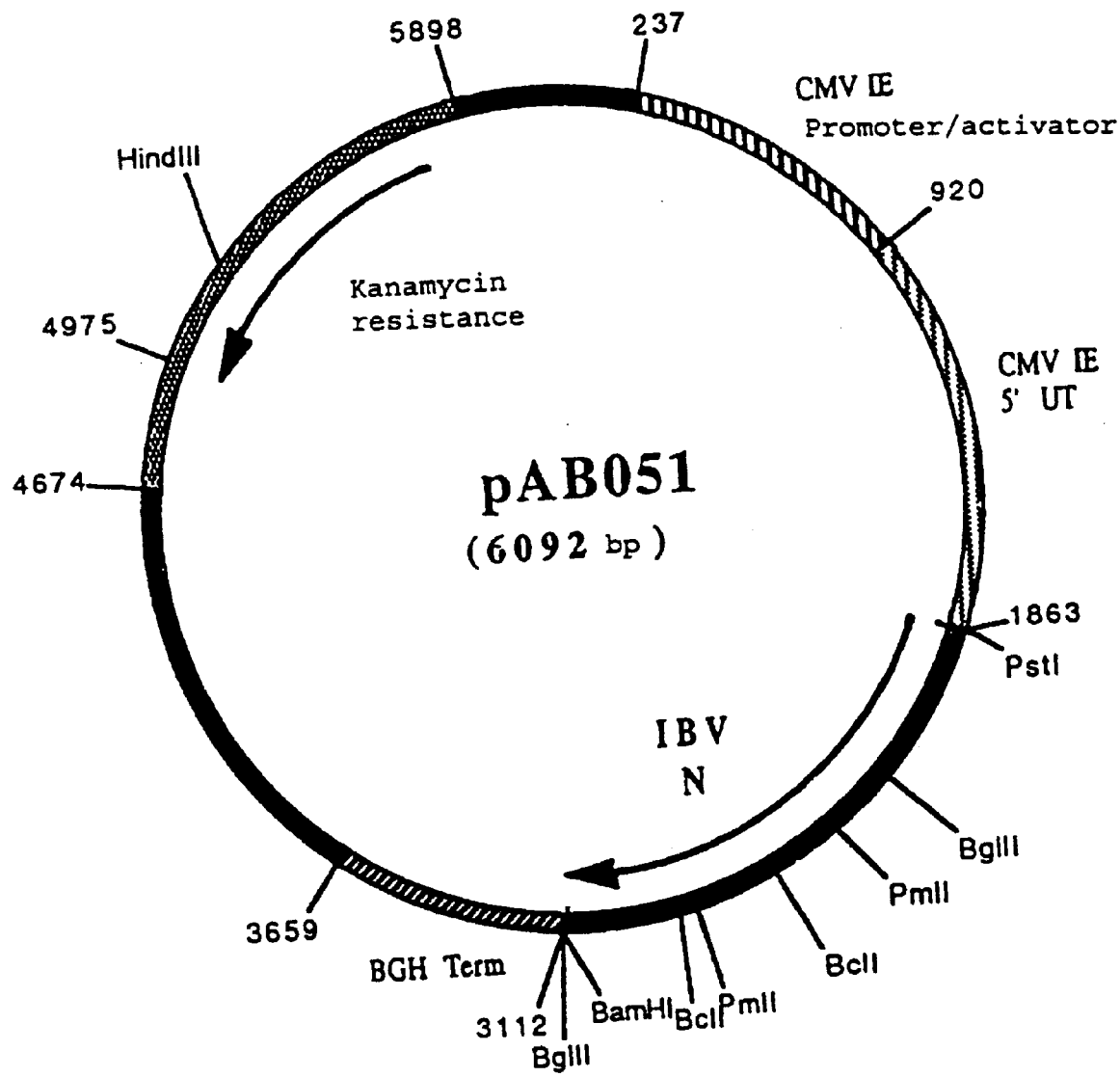
Figure 16:
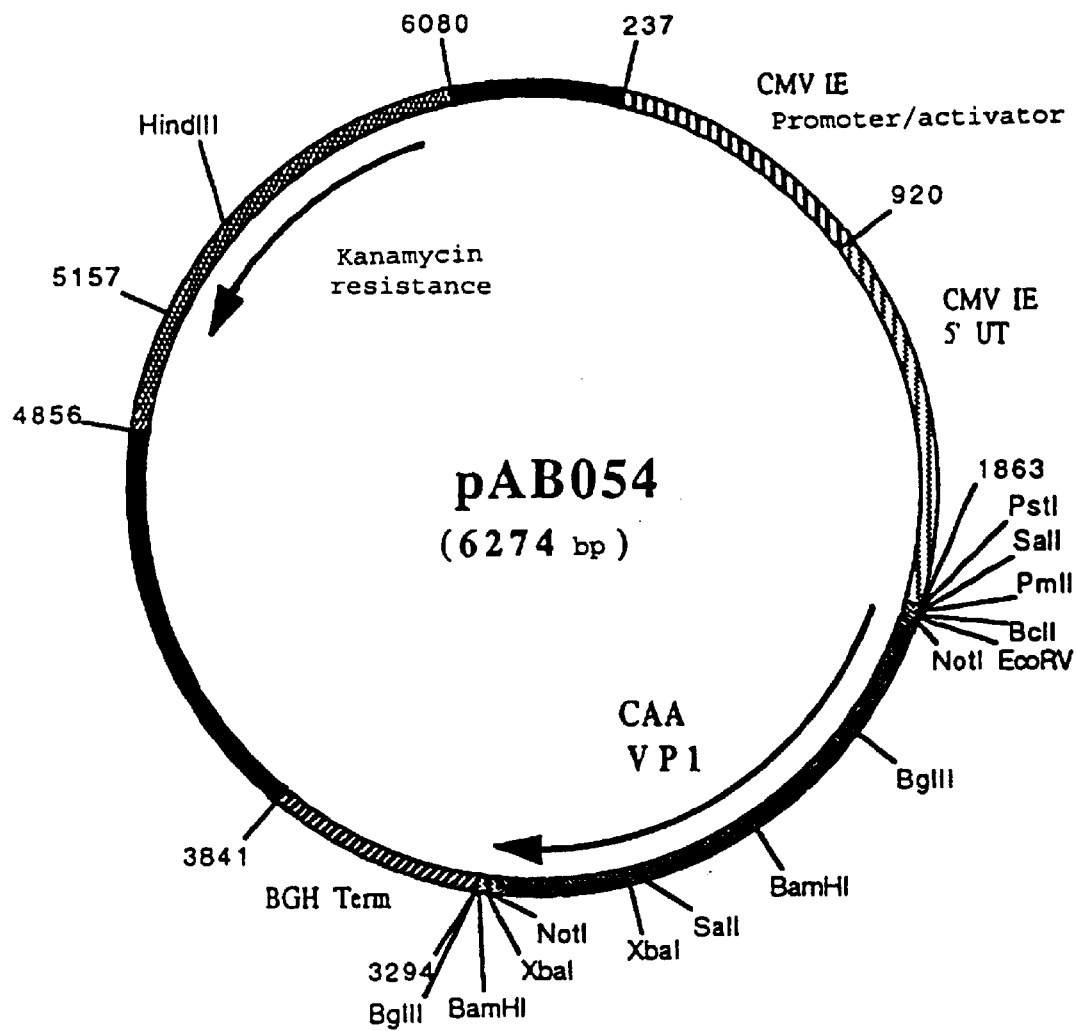
Figure 17:
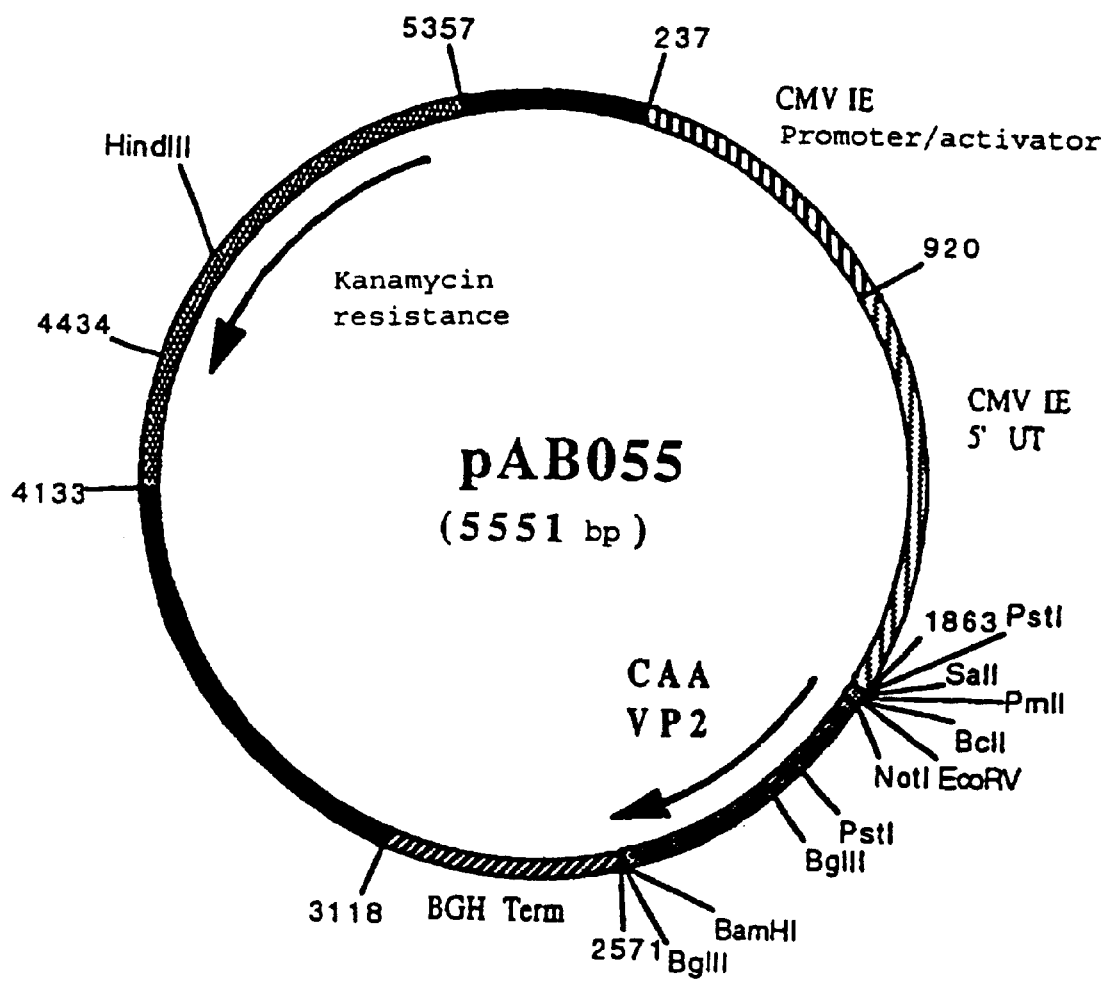
Figure 18:
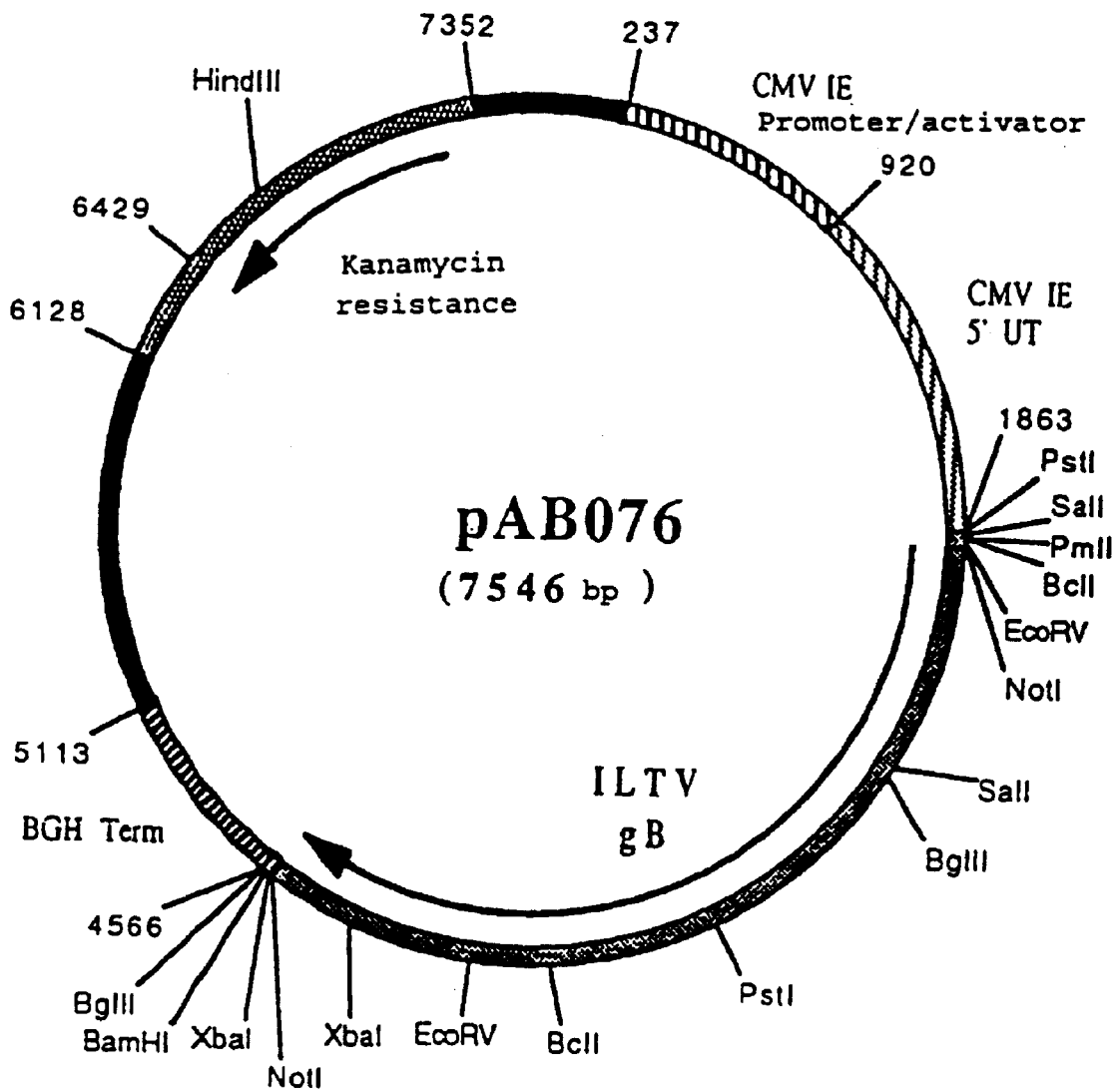
Figure 19:
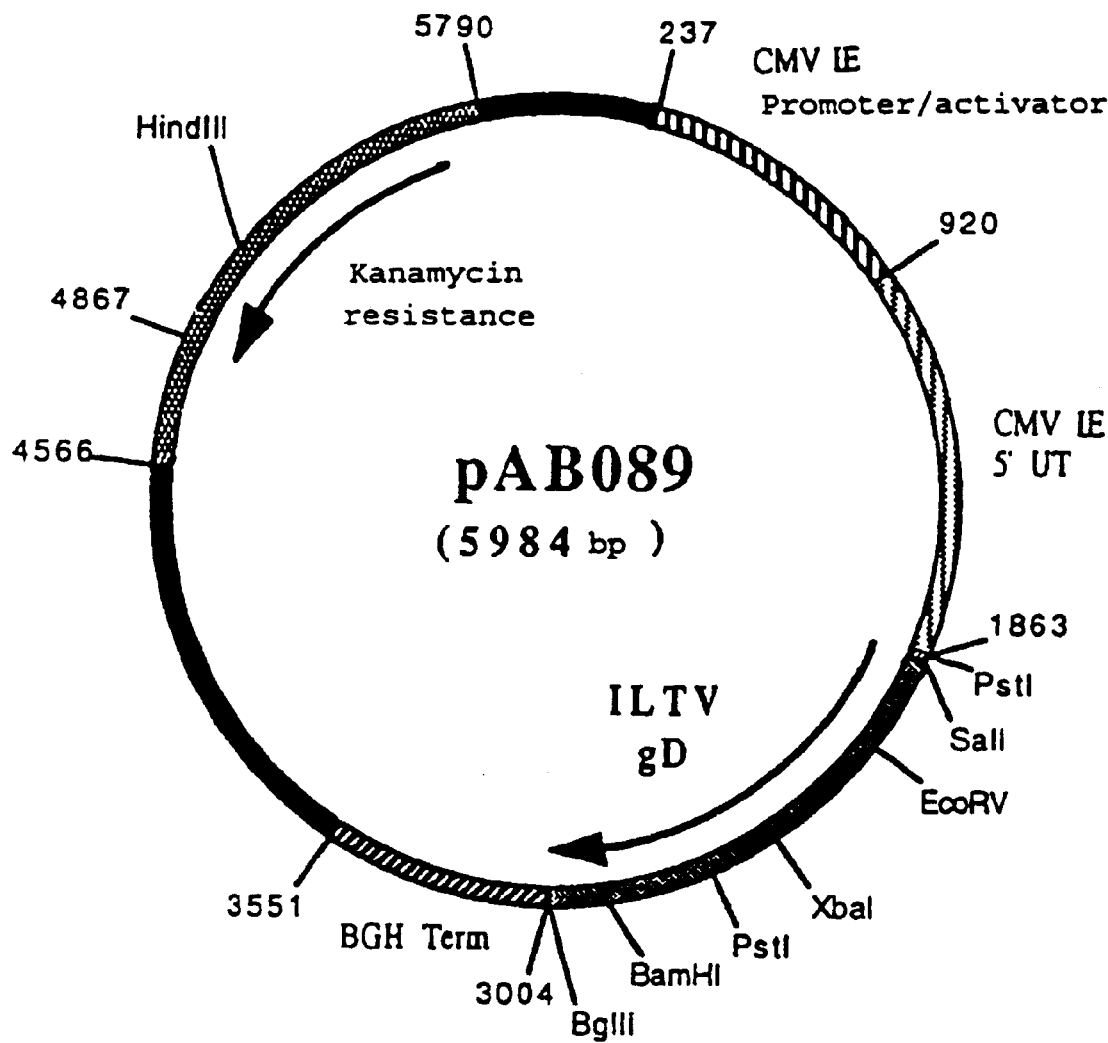
Figure 20:
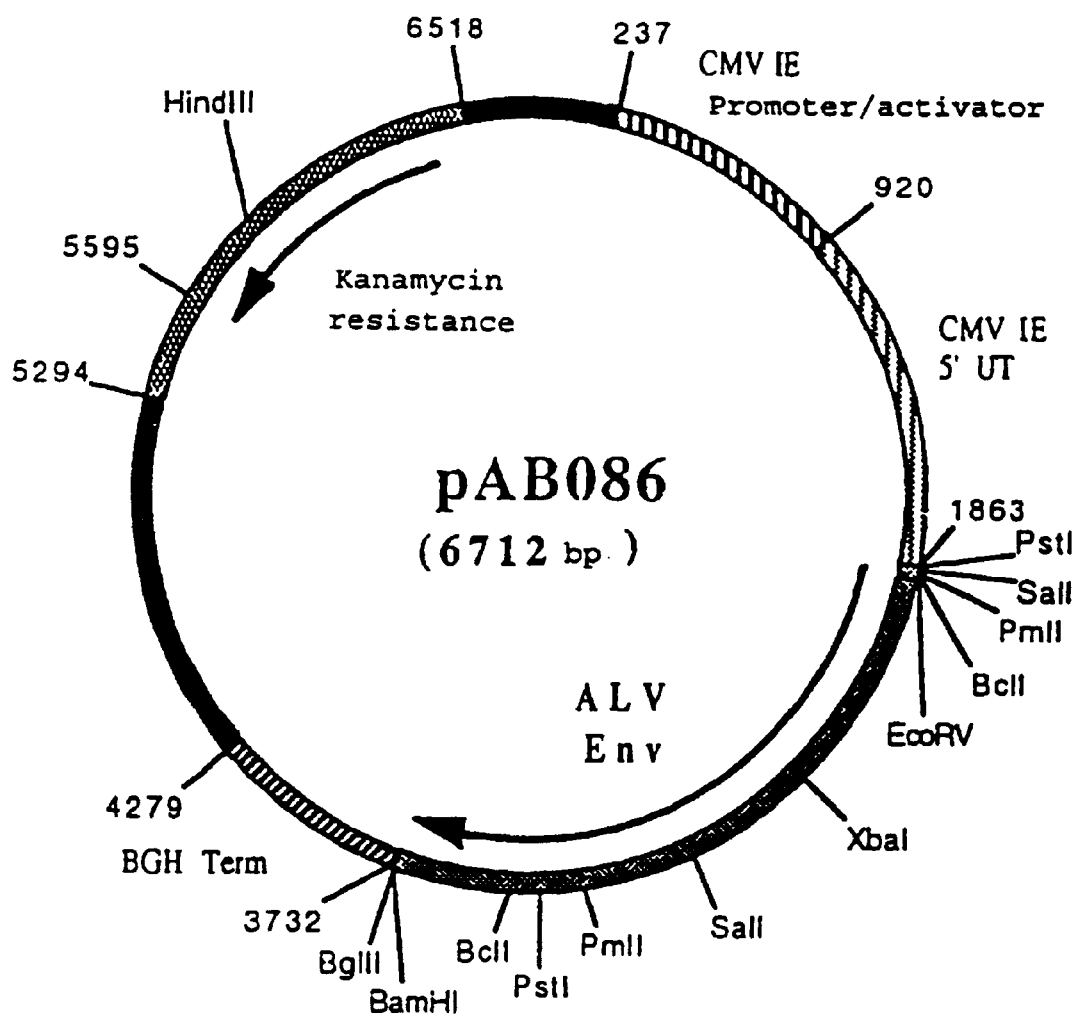
Figure 21:
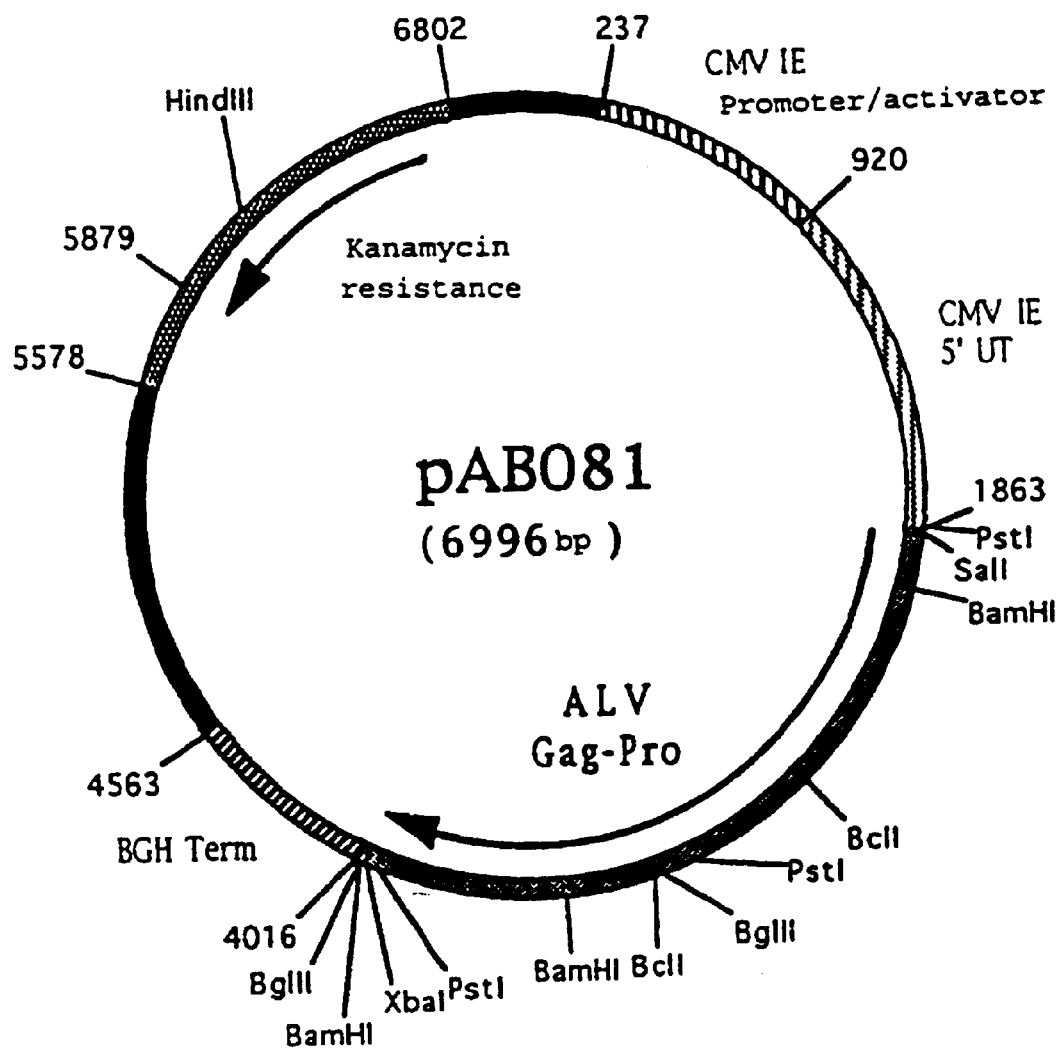
Figure 22:
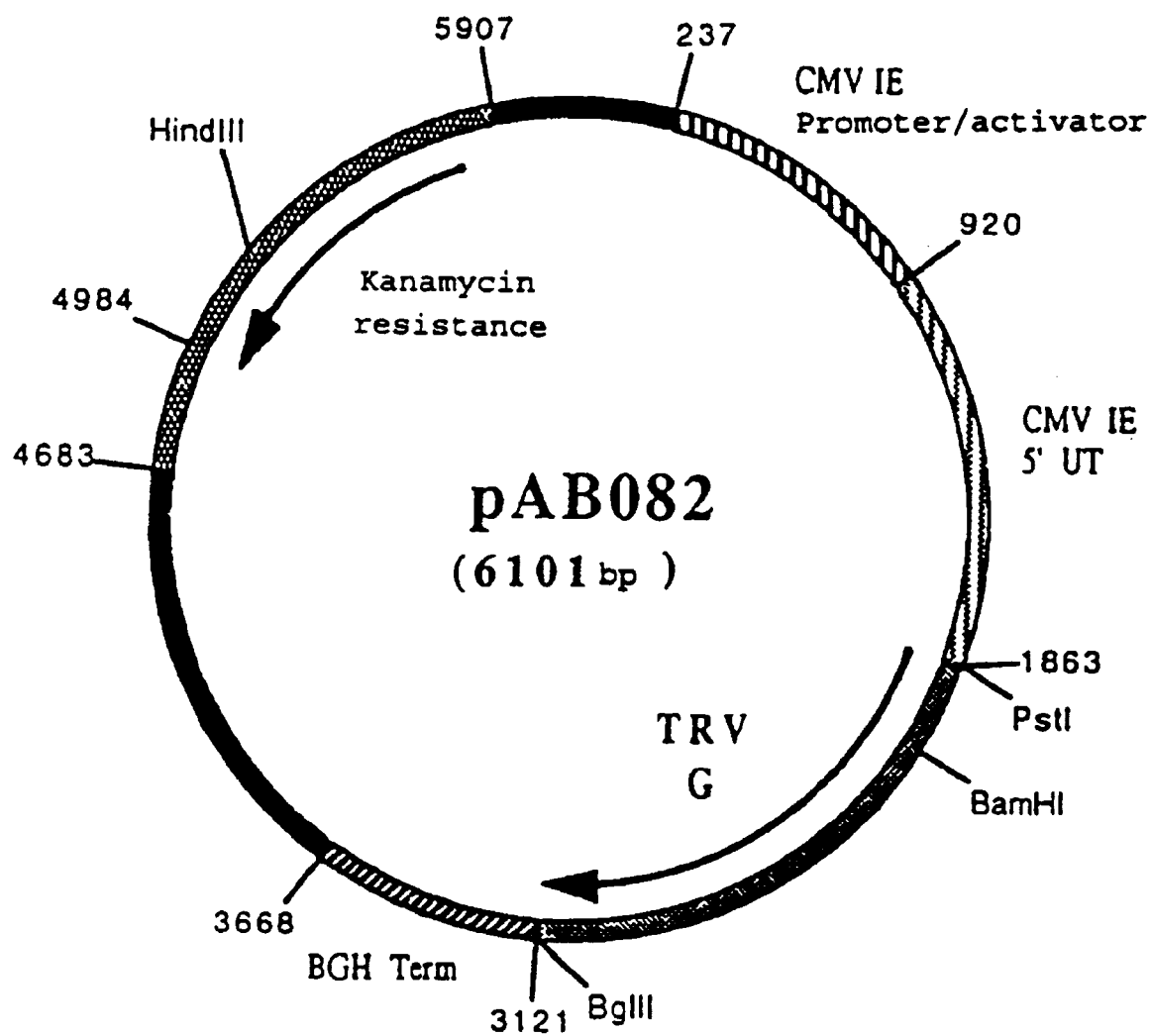
Figure 24:
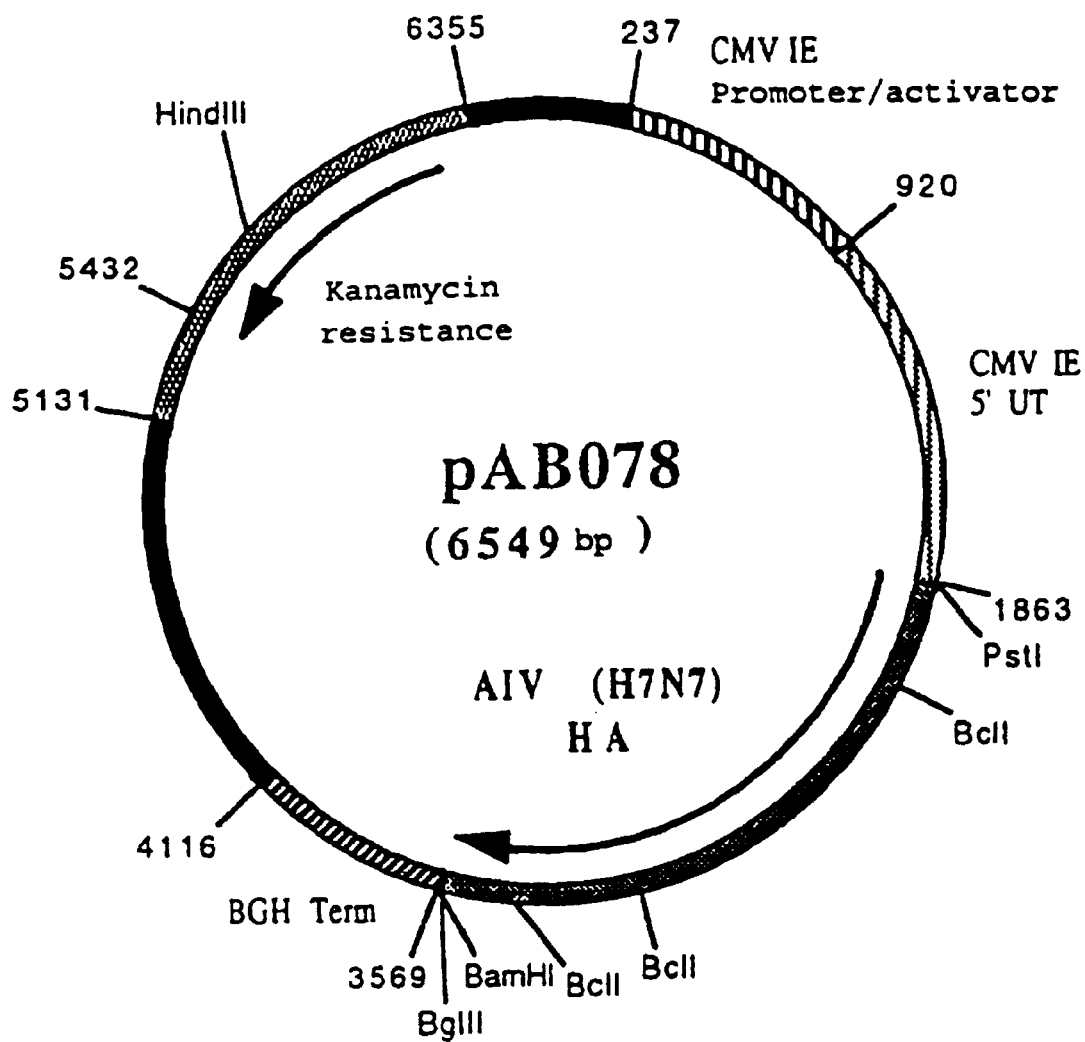
Figure 25:
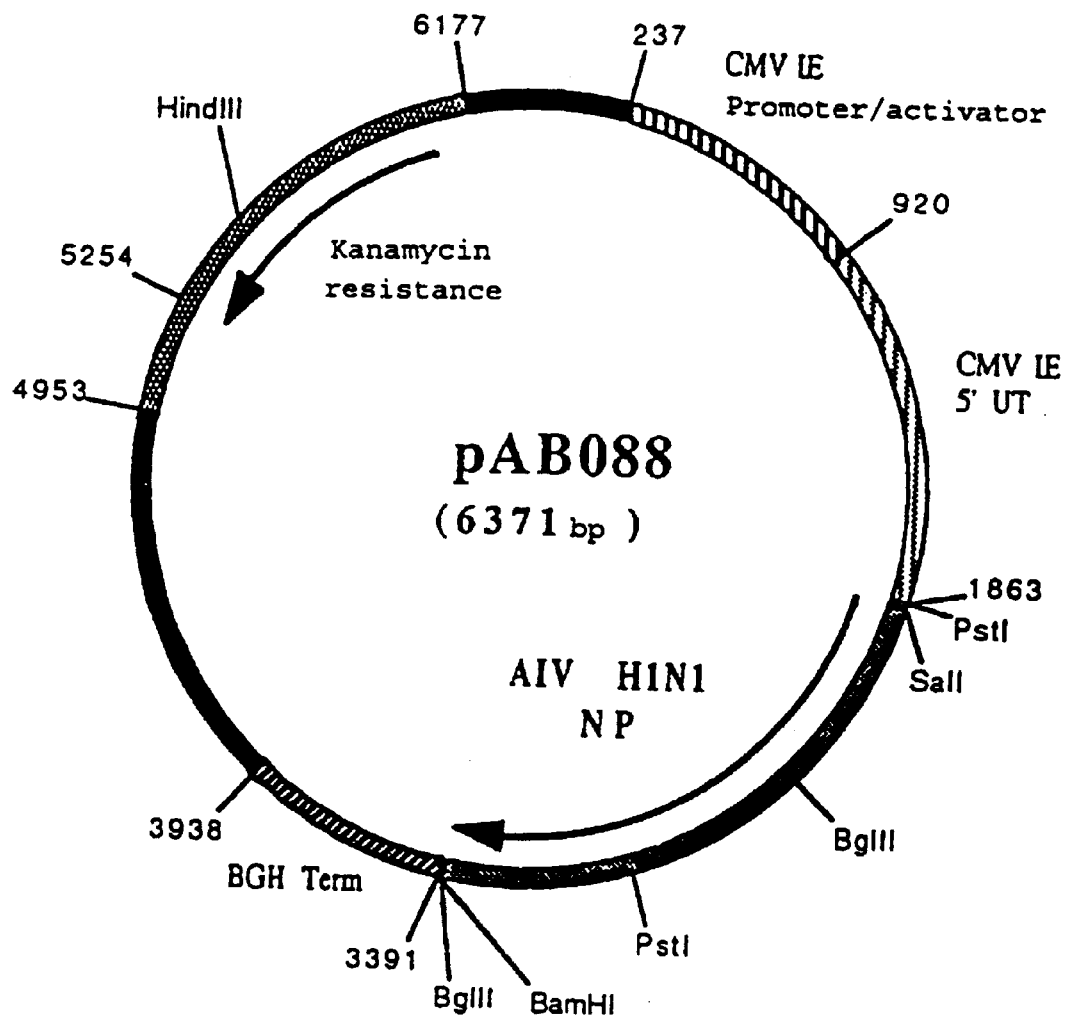

```
   1 ATGGACCGTGCAGTTAGCAGAGTTGCGCTAGAGAATGAAGAAAGAGAAGCAAAGAATACATGG
   1▶MetAspArgAlaValSerArgValAlaLeuGluAsnGluGluArgGluAlaLysAsnThrTrp
  64 CGCTTTGTATTCCGGATTGCAATCTTACTTTTAATAGTAACAACCTTAGCCATCTCTGCAACC
  22▶ArgPheValPheArgIleAlaIleLeuLeuLeuIleValThrThrLeuAlaIleSerAlaThr
 127 GCCCTGGTATATAGCATGGAGGCTAGCACGCCTGGCGACCTTGTTGGCATACCGACTATGATC
  43▶AlaLeuValTyrSerMetGluAlaSerThrProGlyAspLeuValGlyIleProThrMetIle
 190 TCTAAGGCAGAAGAAAAGATTACATCTGCACTCAGTTCTAATCAAGATGTAGTAGATAGGATA
  64▶SerLysAlaGluGluLysIleThrSerAlaLeuSerSerAsnGlnAspValValAspArgIle
 253 TATAAGCAGGTGGCCCTTGAGTCTCCATTGGCGTTGCTAAACACTGAATCTGTAATTATGAAT
  85▶TyrLysGlnValAlaLeuGluSerProLeuAlaLeuLeuAsnThrGluSerValIleMetAsn
 316 GCAATAACGTCTCTCTCTTATCAAATCAATGGAGCTGCAAATAATAGCGGGTGTGGGCACCT
 106▶AlaIleThrSerLeuSerTyrGlnIleAsnGlyAlaAlaAsnAsnSerGlyCysGlyAlaPro
 379 GTTCATGACCCAGATTATATCGGGGGGATAGGCAAAGAACTTATTGTGGATGACGCTAGTGAT
 127▶ValHisAspProAspTyrIleGlyGlyIleGlyLysGluLeuIleValAspAspAlaSerAsp
 442 GTCACATCATTCTATCCCTCTGCGTTCCAAGAACACCTGAACTTTATCCCGGCACCTACTACA
 148▶ValThrSerPheTyrProSerAlaPheGlnGluHisLeuAsnPheIleProAlaProThrThr
 505 GGATCAGGTTGCACTCGGATACCCTCATTCGACATAAGCGCTACCCACTACTGTTACACTCAC
 169▶GlySerGlyCysThrArgIleProSerPheAspIleSerAlaThrHisTyrCysTyrThrHis
 568 AATGTGATATTATCTGGTTGCAGAGATCACTCACACTCATATCAGTACTTAGCACTTGGCGTG
 190▶AsnValIleLeuSerGlyCysArgAspHisSerHisSerTyrGlnTyrLeuAlaLeuGlyVal
 631 CTTCGGACATCTGCAACAGGGAGGGTATTCTTTTCTACTCTGCGTTCCATCAATTTGGATGAC
 211▶LeuArgThrSerAlaThrGlyArgValPhePheSerThrLeuArgSerIleAsnLeuAspAsp
 694 AGCCAAAATCGGAAGTCTTGCAGTGTGAGTGCAACTCCCTTAGGTTGTGATATGCTGTGCTCT
 232▶SerGlnAsnArgLysSerCysSerValSerAlaThrProLeuGlyCysAspMetLeuCysSer
 757 AAAATCACAGAGACTGAGGAAGAGGATTATAGTTCAATTACGCCTACATCGATGGTGCACGGA
 253▶LysIleThrGluThrGluGluGluAspTyrSerSerIleThrProThrSerMetValHisGly
 820 AGGTTAGGGTTTGACGGTCAATACCATGAGAAGGACTTAGACGTCATAACTTTATTTAAGGAT
 274▶ArgLeuGlyPheAspGlyGlnTyrHisGluLysAspLeuAspValIleThrLeuPheLysAsp
 883 TGGGTGGCAAATTACCCAGGAGTGGGGGGTGGGTCTTTTATTAACAACCGCGTATGGTTCCCA
 295▶TrpValAlaAsnTyrProGlyValGlyGlyGlySerPheIleAsnAsnArgValTrpPhePro
 946 GTCTACGGAGGGCTAAAACCCAATTCGCCTAGTGACACCGCACAAGAAGGGAGATATGTAATA
 316▶ValTyrGlyGlyLeuLysProAsnSerProSerAspThrAlaGlnGluGlyArgTyrValIle
1009 TACAAGCGCTACAATGACACATGCCCAGATGAACAAGATTACCAGATTCGGATGGCTAAGTCT
 337▶TyrLysArgTyrAsnAspThrCysProAspGluGlnAspTyrGlnIleArgMetAlaLysSer
1072 TCATATAAGCCTGGGCGGTTTGGTGGAAAACGCGTACAGCAGGCCATCTTATCTATCAAGGTG
 358▶SerTyrLysProGlyArgPheGlyGlyLysArgValGlnGlnAlaIleLeuSerIleLysVal
1135 TCAACATCTTTGGGCGAGGACCCGGTGCTGACTGTACCGCCTAATACAATCACACTCATGGGG
 379▶SerThrSerLeuGlyGluAspProValLeuThrValProProAsnThrIleThrLeuMetGly
1198 GCCGAACGGAGAGTTCTCACAGTAGGGACATCTCATTTCTTGTACCAGCGAGGGTCTTCATAC
 400▶AlaGluArgArgValLeuThrValGlyThrSerHisPheLeuTyrGlnArgGlySerSerTyr
1261 TTCTCTCCTGCTTTATTATACCCTATGACAGTCAACAACAAACGGCTACTCTTCATAGTCCT
 421▶PheSerProAlaLeuLeuTyrProMetThrValAsnAsnLysThrAlaThrLeuHisSerPro
1324 TACACATTCAATGCTTTCACTAGGCCAGGTAGTGTCCCTTGTCAGGCATCAGCAAGATGCCCC
 442▶TyrThrPheAsnAlaPheThrArgProGlySerValProCysGlnAlaSerAlaArgCysPro
1387 AACTCATGTGTCACTGGAGTTTATACTGATCCGTATCCCTTAGTCTTCCATAGGAACCATACC
 463▶AsnSerCysValThrGlyValTyrThrAspProTyrProLeuValPheHisArgAsnHisThr
1450 TTGCGGGGGGTATTCGGGACAATGCTTGATGATGAACAAGCAAGACTTAACCCTGTATCTGCA
 484▶LeuArgGlyValPheGlyThrMetLeuAspAspGluGlnAlaArgLeuAsnProValSerAla
1513 GTATTTGATAACATATCCCGCAGTCGCATAACCCGGGTAAGTTCAAGCCGTACTAAGGCAGCA
 505▶ValPheAspAsnIleSerArgSerArgIleThrArgValSerSerSerArgThrLysAlaAla
```

FIG. 4A  FIG. 4 FIG. 4A / FIG. 4B

1576 TACACGACATCGACATGTTTTAAAGTTGTCAAGACCAATAAAACATATTGCCTCAGCATTGCA
526▶ TyrThrThrSerThrCysPheLysValValLysThrAsnLysThrTyrCysLeuSerIleAla
1639 GAAATATCCAATACCCTCTTCGGGGAATTCAGGATCGTTCCTTTACTAGTTGAGATTCTCAAG
547▶ GluIleSerAsnThrLeuPheGlyGluPheArgIleValProLeuLeuValGluIleLeuLys
1702 GATGATGGGATTTAA
568▶ AspAspGlyIle•••

FIG. 4B

| FIG. 4 | FIG. 4A |
|--------|---------|
|        | FIG. 4B |

```
   1 ATGGGCTCCAGATCTTCTACCAGGATCCCGGTACCTCTAATGCTGATCATCCGAACCGCGCTG
   1▶ MetGlySerArgSerSerThrArgIleProValProLeuMetLeuIleIleArgThrAlaLeu
  64 ACACTGAGCTGTATCCGTCTGACAAGCTCTCTTGATGGCAGGCCTCTTGCGGCTGCAGGGATC
  22▶ ThrLeuSerCysIleArgLeuThrSerSerLeuAspGlyArgProLeuAlaAlaAlaGlyIle
 127 GTGGTAACAGGAGATAAAGCAGTCAACATATACACCTCATCCCAGACAGGGTCAATCATAGTT
  43▶ ValValThrGlyAspLysAlaValAsnIleTyrThrSerSerGlnThrGlySerIleIleVal
 190 AAGTTACTCCCGAATATGCCCAAGGACAAAGAGGTGTGTGCAAAAGCCCCATTGGAGGCATAC
  64▶ LysLeuLeuProAsnMetProLysAspLysGluValCysAlaLysAlaProLeuGluAlaTyr
 253 AACAGGACACTGACTACTTTACTCACCCCCCTTGGTGATTCTATCCGCAGGATACAAGAGTCT
  85▶ AsnArgThrLeuThrThrLeuLeuThrProLeuGlyAspSerIleArgArgIleGlnGluSer
 316 GTGACTACTTCCGGAGGAAGGAGACAGAGACGCTTTATAGGTGCCATTATCGGCAGTGTAGCT
 106▶ ValThrThrSerGlyGlyArgArgGlnArgArgPheIleGlyAlaIleIleGlySerValAla
 379 CTTGGGGTTGCGACAGCTGCACAGATAACAGCAGCTTCGGCCCTGATACAAGCCAACCAGAAT
 127▶ LeuGlyValAlaThrAlaAlaGlnIleThrAlaAlaSerAlaLeuIleGlnAlaAsnGlnAsn
 442 GCTGCCAACATCCTCCGGCTTAAAGAGAGCATTGCTGCAACCAATGAAGCTGTGCACGAGGTC
 148▶ AlaAlaAsnIleLeuArgLeuLysGluSerIleAlaAlaThrAsnGluAlaValHisGluVal
 505 ACTGACGGATTATCACAACTAGCAGTGGCAGTAGGGAAGATGCAACAGTTTGTCAATGACCAG
 169▶ ThrAspGlyLeuSerGlnLeuAlaValAlaValGlyLysMetGlnGlnPheValAsnAspGln
 568 TTCAATAATACAGCGCAAGAATTGGACTGTATAAAAATTGCACAGCAGGTCGGTGTAGAACTC
 190▶ PheAsnAsnThrAlaGlnGluLeuAspCysIleLysIleAlaGlnGlnValGlyValGluLeu
 631 AACTTGTACCTAACTGAATTGACTACAGTATTTGGGCCACAAATCACTTCCCCTGCCTTAACT
 211▶ AsnLeuTyrLeuThrGluLeuThrThrValPheGlyProGlnIleThrSerProAlaLeuThr
 694 CAGCTGACTATCCAAGCGCTTTACAATCTAGCTGGTGGTAATATGGATTACTTGCTGACTAAG
 232▶ GlnLeuThrIleGlnAlaLeuTyrAsnLeuAlaGlyGlyAsnMetAspTyrLeuLeuThrLys
 757 TTAGGTGTAGGGAACAACCAACTCAGCTCATTAATTGGTAGCGGCTTGATCACCGGCAACCCT
 253▶ LeuGlyValGlyAsnAsnGlnLeuSerSerLeuIleGlySerGlyLeuIleThrGlyAsnPro
 820 ATTCTGTACGACTCACAGACTCAGATCTTGGGTATACAGGTAACTTTGCCTTCAGTTGGGAAC
 274▶ IleLeuTyrAspSerGlnThrGlnIleLeuGlyIleGlnValThrLeuProSerValGlyAsn
 883 CTGAATAATATGCGTGCCACCTACCTGGAGACCTTATCTGTAAGCACAACCAAGGGATTTGCC
 295▶ LeuAsnAsnMetArgAlaThrTyrLeuGluThrLeuSerValSerThrThrLysGlyPheAla
 946 TCAGCACTTGTCCCAAAAGTGGTGACACAGGTCGGTTCCGTGATAGAAGAACTTGACACCTCA
 316▶ SerAlaLeuValProLysValValThrGlnValGlySerValIleGluGluLeuAspThrSer
1009 TACTGTATAGGGACCGACTTGGATTTATACTGTACAAGAATAGTGACATTCCCTATGTCTCCT
 337▶ TyrCysIleGlyThrAspLeuAspLeuTyrCysThrArgIleValThrPheProMetSerPro
1072 GGTATTTATTCTTGTCTGAGCGGTAATACATCGGCTTGCATGTATTCAAAGACTGAAGGCGCA
 358▶ GlyIleTyrSerCysLeuSerGlyAsnThrSerAlaCysMetTyrSerLysThrGluGlyAla
1135 CTTACTACGCCATATATGGCTCTCAAAGGCTCAGTTATTGCCAATTGCAAGCTGACAACATGT
 379▶ LeuThrThrProTyrMetAlaLeuLysGlySerValIleAlaAsnCysLysLeuThrThrCys
1198 AGATGTGCAGATCCCCCAGGTATCATATCGCAAAATTATGGAGAAGCTGTGTCCTTAATAGAT
 400▶ ArgCysAlaAspProProGlyIleIleSerGlnAsnTyrGlyGluAlaValSerLeuIleAsp
1261 AGGCACTCATGCAACGTCTTATCCTTAGACGGGATAACTCTGAGGCTCAGTGGGGAATTTGAT
 421▶ ArgHisSerCysAsnValLeuSerLeuAspGlyIleThrLeuArgLeuSerGlyGluPheAsp
1324 GCAACCTATCAAAAGAATATCTCTATACTAGATTCTCAAGTTATAGTGACAGGCAATCTTGAT
 442▶ AlaThrTyrGlnLysAsnIleSerIleLeuAspSerGlnValIleValThrGlyAsnLeuAsp
1387 ATATCAACTGAGCTTGGGAATGTCAACAACTCAATAAGTAATGCCCTGAATAAGTTAGAGGAA
 463▶ IleSerThrGluLeuGlyAsnValAsnAsnSerIleSerAsnAlaLeuAsnLysLeuGluGlu
1450 AGCAACAGCAAACTAGACAAAGTCAATGTCAAACTGACCAGCACATCTGCTCTCATTACCTAC
 484▶ SerAsnSerLysLeuAspLysValAsnValLysLeuThrSerThrSerAlaLeuIleThrTyr
1513 ATCGTTTTAACTGTCATATCTCTTGTTTTGGTGTACTTAGCCTGGTTCTAGCATGCTACCTG
 505▶ IleValLeuThrValIleSerLeuValPheGlyValLeuSerLeuValLeuAlaCysTyrLeu
1576 ATGTACAAGCAAAAGGCACAACAAAAGACCTTGTTATGGCTTGGGAATAATACCCTTGATCAG
 526▶ MetTyrLysGlnLysAlaGlnGlnLysThrLeuLeuTrpLeuGlyAsnAsnThrLeuAspGln
1639 ATGAGAGCCACTACAAAAATATGA
 547▶ MetArgAlaThrThrLysIle···
```

FIG. 6

```
   1 ATGACAAACCTGCAAGATCAAACCCAACAGATTGTTCCGTTCATACGGAGCCTTCTGATGCCA
   1▶ MetThrAsnLeuGlnAspGlnThrGlnGlnIleValProPheIleArgSerLeuLeuMetPro
  64 ACAACCGGACCGGCGTCCATTCCGGACGACACCCTGGAGAAGCACACTCTCAGGTCAGAGACC
  22▶ ThrThrGlyProAlaSerIleProAspAspThrLeuGluLysHisThrLeuArgSerGluThr
 127 TCGACCTACAATTTGACTGTGGGGGACACAGGGTCAGGGCTAATTGTCTTTTTCCCTGGATTC
  43▶ SerThrTyrAsnLeuThrValGlyAspThrGlySerGlyLeuIleValPhePheProGlyPhe
 190 CCTGGCTCAATTGTGGGTGCTCACTACACACTGCAGAGCAATGGGAACTACAAGTTCGATCAG
  64▶ ProGlySerIleValGlyAlaHisTyrThrLeuGlnSerAsnGlyAsnTyrLysPheAspGln
 253 ATGCTCCTGACTGCCCAGAACCTACCGGCCAGCTACAACTACTGCAGACTAGTGAGTCGGAGT
  85▶ MetLeuLeuThrAlaGlnAsnLeuProAlaSerTyrAsnTyrCysArgLeuValSerArgSer
 316 CTCACAGTGAGGTCAAGCACACTCCCTGGTGGCGTTTATGCACTAAACGGCACCATAAACGCC
 106▶ LeuThrValArgSerSerThrLeuProGlyGlyValTyrAlaLeuAsnGlyThrIleAsnAla
 379 GTGACCTTCCAAGGAAGCCTGAGTGAACTGACAGATGTTAGCTACAATGGGTTGATGTCTGCA
 127▶ ValThrPheGlnGlySerLeuSerGluLeuThrAspValSerTyrAsnGlyLeuMetSerAla
 442 ACAGCCAACATCAACGACAAAATTGGGAATGTCCTGGTAGGGGAAGGGGTCACTGTCCTCAGC
 148▶ ThrAlaAsnIleAsnAspLysIleGlyAsnValLeuValGlyGluGlyValThrValLeuSer
 505 CTACCCACATCATATGATCTTGGGTATGTGAGGCTTGGTGACCCCATTCCCGCTATAGGGCTT
 169▶ LeuProThrSerTyrAspLeuGlyTyrValArgLeuGlyAspProIleProAlaIleGlyLeu
 568 GACCCAAAAATGGTAGCTACATGCGACAGCAGTGACAGGCCCAGAGTCTACACCATAACTGCA
 190▶ AspProLysMetValAlaThrCysAspSerSerAspArgProArgValTyrThrIleThrAla
 631 GCCGATGATTACCAATTCTCATCACAGTACCAACCAGGTGGGGTAACAATCACACTGTTCTCA
 211▶ AlaAspAspTyrGlnPheSerSerGlnTyrGlnProGlyGlyValThrIleThrLeuPheSer
 694 GCCAACATTGATGCTATCACAAGCCTCAGCATTGGGGGAGAGCTCGTGTTTCAAACAAGCGTC
 232▶ AlaAsnIleAspAlaIleThrSerLeuSerIleGlyGlyGluLeuValPheGlnThrSerVal
 757 CAAGGCCTTGTACTGGGCGCCACCATCTACCTTATAGGCTTTGATGGGACTGCGGTAATCACC
 253▶ GlnGlyLeuValLeuGlyAlaThrIleTyrLeuIleGlyPheAspGlyThrAlaValIleThr
 820 AGAGCTGTAGCCGCAGATAATGGGCTGACGGCCGGCACCGACAATCTTATGCCATTCAATCTT
 274▶ ArgAlaValAlaAlaAspAsnGlyLeuThrAlaGlyThrAspAsnLeuMetProPheAsnLeu
 883 GTCATTCCAACCAATGAGATAACCCAGCCAATCACATCCATCAAACTGGAGATAGTGACCTCC
 295▶ ValIleProThrAsnGluIleThrGlnProIleThrSerIleLysLeuGluIleValThrSer
 946 AAAAGTGGTGGTCAGGCAGGGGATCAGATGTCATGGTCGGCAAGTGGGAGCCTAGCAGTGACG
 316▶ LysSerGlyGlyGlnAlaGlyAspGlnMetSerTrpSerAlaSerGlySerLeuAlaValThr
1009 ATCCATGGTGGCAACTATCCAGGGGCCCTCCGTCCCGTCACACTAGTAGCCTACGAAAGAGTG
 337▶ IleHisGlyGlyAsnTyrProGlyAlaLeuArgProValThrLeuValAlaTyrGluArgVal
1072 GCAACAGGATCCGTCGTTACGGTCGCTGGGGTGAGTAACTTCGAGCTGATTCCAAATCCTGAA
 358▶ AlaThrGlySerValValThrValAlaGlyValSerAsnPheGluLeuIleProAsnProGlu
1135 CTAGCAAAGAACCTGGTTACAGAATACGGCCGATTTGACCCAGGAGCCATGAACTACACAAAA
 379▶ LeuAlaLysAsnLeuValThrGluTyrGlyArgPheAspProGlyAlaMetAsnTyrThrLys
1198 TTGATACTGAGTGAGAGGGACCGTCTTGGCATCAAGACCGTCTGGCCAACAAGGGAGTACACT
 400▶ LeuIleLeuSerGluArgAspArgLeuGlyIleLysThrValTrpProThrArgGluTyrThr
1261 GATTTTCGTGAGTACTTCATGGAGGTGGCCGACCTCAACTCTCCCCTGAAGATTGCAGGAGCA
 421▶ AspPheArgGluTyrPheMetGluValAlaAspLeuAsnSerProLeuLysIleAlaGlyAla
1324 TTTGGCTTCAAAGACATAATCCGGGCTATAAGGAGGTAA
 442▶ PheGlyPheLysAspIleIleArgAlaIleArgArg···
```

FIG. 8

```
  1 ATGTTGGTAACACCTCTTTTACTAGTGACTCTTTTGTGTGTACTATGTAGTGCTGCTTTGTAT
  1▶MetLeuValThrProLeuLeuLeuValThrLeuLeuCysValLeuCysSerAlaAlaLeuTyr

64 GACAGTAGTTCTTACGTTTACTACTACCAAAGTGCCTTTAGACCACCTAATGGTTGGCATTTA
 22▶AspSerSerSerTyrValTyrTyrTyrGlnSerAlaPheArgProProAsnGlyTrpHisLeu

127 CACGGGGGTGCTTATGCGGTAGTTAATATTTCTAGCGAATCTAATAATGCAGGCTCTTCACCT
 43▶HisGlyGlyAlaTyrAlaValValAsnIleSerSerGluSerAsnAsnAlaGlySerSerPro

190 GGGTGTATTGTTGGTACTATTCATGGTGGTCGTGTTGTTAATGCTTCTTCTATAGCTATGACG
 64▶GlyCysIleValGlyThrIleHisGlyGlyArgValValAsnAlaSerSerIleAlaMetThr

253 GCACCGTCATCAGGTATGGCTTGGTCTAGCAGTCAGTTTTGTACTGCACACTGTAACTTTTCA
 85▶AlaProSerSerGlyMetAlaTrpSerSerSerGlnPheCysThrAlaHisCysAsnPheSer

316 GATACTACAGTGTTTGTTACACATTGTTATAAATATGATGGGTGTCCTATAACTGGCATGCTT
106▶AspThrThrValPheValThrHisCysTyrLysTyrAspGlyCysProIleThrGlyMetLeu

379 CAAAAGAATTTTTTACGTGTTTCTGCTATGAAAAATGGCCAGCTTTTCTATAATTTAACAGTT
127▶GlnLysAsnPheLeuArgValSerAlaMetLysAsnGlyGlnLeuPheTyrAsnLeuThrVal

442 AGTGTAGCTAAGTACCCTACTTTTAAATCATTTCAGTGTGTTAATAATTTAACATCCGTATAT
148▶SerValAlaLysTyrProThrPheLysSerPheGlnCysValAsnAsnLeuThrSerValTyr

505 TTAAATGGTGATCTTGTTTACACCTCTAATGAGACCACAGATGTTACATCTGCAGGTGTTTAT
169▶LeuAsnGlyAspLeuValTyrThrSerAsnGluThrThrAspValThrSerAlaGlyValTyr

568 TTTAAAGCTGGTGGACCTATAACTTATAAAGTTATGAGAGAAGTTAAAGCCCTGGCTTATTTT
190▶PheLysAlaGlyGlyProIleThrTyrLysValMetArgGluValLysAlaLeuAlaTyrPhe

631 GTTAATGGTACTGCACAAGATGTTATTTTGTGTGATGGATCACCTAGAGGCTTGTTAGCATGC
211▶ValAsnGlyThrAlaGlnAspValIleLeuCysAspGlySerProArgGlyLeuLeuAlaCys

694 CAGTATAATACTGGCAATTTTTCAGATGGCTTTTATCCTTTTATTAATAGTAGTTTAGTTAAG
232▶GlnTyrAsnThrGlyAsnPheSerAspGlyPheTyrProPheIleAsnSerSerLeuValLys

757 CAGAAGTTTATTGTCTATCGTGAAAATAGTGTTAATACTACTTTTACGTTACACAATTTCACT
253▶GlnLysPheIleValTyrArgGluAsnSerValAsnThrThrPheThrLeuHisAsnPheThr

820 TTTCATAATGAGACTGGCGCCAACCCTAATCCTAGTGGTGTTCAGAATATTCTAACTTACCAA
274▶PheHisAsnGluThrGlyAlaAsnProAsnProSerGlyValGlnAsnIleLeuThrTyrGln

883 ACACAAACAGCTCAGAGTGGTTATTATAATTTTAATTTTTCCTTTCTGAGTAGTTTTGTTTAT
295▶ThrGlnThrAlaGlnSerGlyTyrTyrAsnPheAsnPheSerPheLeuSerSerPheValTyr

946 AAGGAGTCTAATTTTATGTATGGATCTTATCACCCAAGTTGTAATTTTAGACTAGAAACTATT
316▶LysGluSerAsnPheMetTyrGlySerTyrHisProSerCysAsnPheArgLeuGluThrIle

1009 AATAATGGCTTGTGGTTTAATTCACTTTCAGTTTCAATTGCTTACGGTCCTCTTCAAGGTGGT
337▶AsnAsnGlyLeuTrpPheAsnSerLeuSerValSerIleAlaTyrGlyProLeuGlnGlyGly
```

FIG. 10A

| FIG. 10 | FIG. 10A |
| --- | --- |
|  | FIG. 10B |

1072 TGCAAGCAATCTGTCTTTAGTGGTAGAGCAACTTGTTGTTATGCTTATTCATATGGAGGTCCT
358▶ CysLysGlnSerValPheSerGlyArgAlaThrCysCysTyrAlaTyrSerTyrGlyGlyPro

1135 TCGCTGTGTAAAGGTGTTTATTCAGGTGAGTTAGCTCTTAATTTTGAATGTGGACTGTTAGTT
379▶ SerLeuCysLysGlyValTyrSerGlyGluLeuAlaLeuAsnPheGluCysGlyLeuLeuVal

1198 TATGTTACTAAGAGCGGTGGCTCTCGTATACAAACAGCCACTGAACCGCCAGTTATAACTCGA
400▶ TyrValThrLysSerGlyGlySerArgIleGlnThrAlaThrGluProProValIleThrArg

1261 CACAATTATAATAATATTACTTTAAATACTTGTGTTGATTATAATATATATGGCAGAACTGGC
421▶ HisAsnTyrAsnAsnIleThrLeuAsnThrCysValAspTyrAsnIleTyrGlyArgThrGly

1324 CAAGGTTTTATTACTAATGTAACCGACTCAGCTGTTAGTTATAATTATCTAGCAGACGCAGGT
442▶ GlnGlyPheIleThrAsnValThrAspSerAlaValSerTyrAsnTyrLeuAlaAspAlaGly

1387 TTGGCTATTTTAGATACATCTGGTTCCATAGACATCTTTGTTGTACAAGGTGAATATGGTCTT
463▶ LeuAlaIleLeuAspThrSerGlySerIleAspIlePheValValGlnGlyGluTyrGlyLeu

1450 ACTTATTATAAGGTTAACCCTTGCGAAGATGTCAACCAGCAGTTTGTAGTTTCTGGTGGTAAA
484▶ ThrTyrTyrLysValAsnProCysGluAspValAsnGlnGlnPheValValSerGlyGlyLys

1513 TTAGTAGGTATTCTTACTTCACGTAATGAGACTGGTTCTCAGCTTCTTGAGAACCAGTTTTAC
505▶ LeuValGlyIleLeuThrSerArgAsnGluThrGlySerGlnLeuLeuGluAsnGlnPheTyr

1576 ATTAAAATCACTAATGGAACACGTCGTTTTAGACGTTAA
526▶ IleLysIleThrAsnGlyThrArgArgPheArgArg···

FIG. 10B

| FIG. 10 | FIG. 10A |
|---------|----------|
|         | FIG. 10B |

```
  1 ATGTCCAACGAGACAAATTGTACTCTTGACTTTGAACAGTCAGTTGAGCTTTTTAAAGAGTAT
  1▶MetSerAsnGluThrAsnCysThrLeuAspPheGluGlnSerValGluLeuPheLysGluTyr

64 AATTTATTTATAACTGCATTCTTGTTGTTCTTAACCATAATACTTCAGTATGGCTATGCAACA
 22▶AsnLeuPheIleThrAlaPheLeuLeuPheLeuThrIleIleLeuGlnTyrGlyTyrAlaThr

127 AGAAGTAAGTTTATTTATATACTGAAAATGATAGTGTTATGGTGCTTTTGGCCCCTTAACATT
 43▶ArgSerLysPheIleTyrIleLeuLysMetIleValLeuTrpCysPheTrpProLeuAsnIle

190 GCAGTAGGTGTAATTTCATGTATATACCCACCAAACACAGGAGGTCTTGTCGCAGCGATAATA
 64▶AlaValGlyValIleSerCysIleTyrProProAsnThrGlyGlyLeuValAlaAlaIleIle

253 CTTACAGTGTTTGCGTGTCTGTCTTTTGTAGGTTATTGGATCCAGAGTATTAGACTCTTTAAG
 85▶LeuThrValPheAlaCysLeuSerPheValGlyTyrTrpIleGlnSerIleArgLeuPheLys

316 CGGTGTAGGTCATGGTGGTCATTTAACCCAGAATCTAATGCCGTAGGTTCAATACTCCTAACT
106▶ArgCysArgSerTrpTrpSerPheAsnProGluSerAsnAlaValGlySerIleLeuLeuThr

379 AATGGTCAACAATGTAATTTTGCTATAGAGAGTGTGCCAATGGTGCTTTCTCCAATTATAAAG
127▶AsnGlyGlnGlnCysAsnPheAlaIleGluSerValProMetValLeuSerProIleIleLys

442 AATGGTGTTCTTTATTGTGAGGGTCAGTGGCTTGCTAAGTGTGAACCAGACCACTTGCCTAAA
148▶AsnGlyValLeuTyrCysGluGlyGlnTrpLeuAlaLysCysGluProAspHisLeuProLys

505 GATATATTTGTTTGTACACCGGATAGACGTAATATCTACCGTATGGTGCAGAAATATACTGGT
169▶AspIlePheValCysThrProAspArgArgAsnIleTyrArgMetValGlnLysTyrThrGly

568 GACCAAAGCGGAAATAAGAAACGGTTTGCTACGTTTGTCTATGCAAAGCAGTCAGTAGATACT
190▶AspGlnSerGlyAsnLysLysArgPheAlaThrPheValTyrAlaLysGlnSerValAspThr

631 GGCGAGCTAGAAAGTGTAGCAACAGGAGGGAGTAGTCTTTACACCTAA
211▶GlyGluLeuGluSerValAlaThrGlyGlySerSerLeuTyrThr***
```

FIG. 12

```
   1 ATGGCAAGCGGTAAGGCAACTGGAAAGACAGACGCCCCAGCTCCAGTCATCAAACTAGGAGGA
   1▶MetAlaSerGlyLysAlaThrGlyLysThrAspAlaProAlaProValIleLysLeuGlyGly
  64 CCAAAGCCACCTAAAGTTGGTTCTTCTGGAAATGTATCTTGGTTTCAAGCAATAAAAGCCAAG
  22▶ProLysProProLysValGlySerSerGlyAsnValSerTrpPheGlnAlaIleLysAlaLys
 127 AAGTTAAATTCACCTCCGCCTAAGTTTGAAGGTAGCGGTGTTCCTGATAATGAAAATCTAAAA
  43▶LysLeuAsnSerProProProLysPheGluGlySerGlyValProAspAsnGluAsnLeuLys
 190 CCAAGTCAGCAGCATGGATATTGGAGACGCCAAGCTAGGTTTAAGCCAGGTAAAGGTGGAAGA
  64▶ProSerGlnGlnHisGlyTyrTrpArgArgGlnAlaArgPheLysProGlyLysGlyGlyArg
 253 AAACCAGTCCCAGATGCTTGGTATTTTTACTATACTGGAACAGGACCAGCCGCTAACCTGAAT
  85▶LysProValProAspAlaTrpTyrPheTyrTyrThrGlyThrGlyProAlaAlaAsnLeuAsn
 316 TGGGGTGATAGCCAAGATGGTATAGTGTGGGTTGCTGGTAAGGGTGCTGATACTAAATTTAGA
 106▶TrpGlyAspSerGlnAspGlyIleValTrpValAlaGlyLysGlyAlaAspThrLysPheArg
 379 TCTAATCAGGGTACTCGTGACTCTGACAAGTTTGACCAATATCCGCTACGGTTTTCAGACGGA
 127▶SerAsnGlnGlyThrArgAspSerAspLysPheAspGlnTyrProLeuArgPheSerAspGly
 442 GGACCTGATGGTAATTTCCGTTGGGATTTCATTCCTCTGAATCGTGGCAGGAGTGGGAGATCA
 148▶GlyProAspGlyAsnPheArgTrpAspPheIleProLeuAsnArgGlyArgSerGlyArgSer
 505 ACAGCAGCTTCATCAGCGGCATCTAGTAGAGCACCATCACGTGAAGTTTCGCGTGGTCGCAGG
 169▶ThrAlaAlaSerSerAlaAlaSerSerArgAlaProSerArgGluValSerArgGlyArgArg
 568 AGTGGTTCTGAAGATGATCTTATTGCTCGTGCAGCAAGGATAATTCAGGATCAGCAGAAGAAG
 190▶SerGlySerGluAspAspLeuIleAlaArgAlaAlaArgIleIleGlnAspGlnGlnLysLys
 631 GGTTCTCGCATTACAAAGGCTAAGGCTGATGAAATGGCTCACCGCCGGTATTGCAAGCGCACT
 211▶GlySerArgIleThrLysAlaLysAlaAspGluMetAlaHisArgArgTyrCysLysArgThr
 694 ATTCCACCTAATTATAAGGTTGATCAAGTGTTTGGTCCCCGTACTAAAGGTAAGGAGGGAAAT
 232▶IleProProAsnTyrLysValAspGlnValPheGlyProArgThrLysGlyLysGluGlyAsn
 757 TTTGGTGATGACAAGATGAATGAGGAAGGTATTAAGGATGGGCGCGTTACAGCAATGCTCAAC
 253▶PheGlyAspAspLysMetAsnGluGluGlyIleLysAspGlyArgValThrAlaMetLeuAsn
 820 CTAGTTCCTAGCAGCCATGCTTGTCTTTTCGGAAGTAGAGTGACGCCCAGACTTCAACCAGAT
 274▶LeuValProSerSerHisAlaCysLeuPheGlySerArgValThrProArgLeuGlnProAsp
 883 GGGCTGCACTTGAAATTTGAATTTACTACTGTGGTCCCACGTGATGATCCGCAGTTTGATAAT
 295▶GlyLeuHisLeuLysPheGluPheThrThrValValProArgAspAspProGlnPheAspAsn
 946 TATGTAAAAATTTGTGATCAGTGTGTTGATGGTGTAGGAACACGTCCAACAGATGATGAACCA
 316▶TyrValLysIleCysAspGlnCysValAspGlyValGlyThrArgProThrAspAspGluPro
1009 AGACCAAAGTCACGCTCAAGTTCAAAACCTGCAACAAGAGGAAATTCTCCAGCGCCAAGACAG
 337▶ArgProLysSerArgSerSerSerLysProAlaThrArgGlyAsnSerProAlaProArgGln
1072 CAGCGCCCTAAGAAGGAGAAAAAGCCAAAGAAGCAGGATGATGAAGTGGATAAAGCATTGACC
 358▶GlnArgProLysLysGluLysLysProLysLysGlnAspAspGluValAspLysAlaLeuThr
1135 TCAGATGAGGAGAGGAACAATGCACAGCTGGAATTTGATGATGAACCCAAGGTAATTAACTGG
 379▶SerAspGluGluArgAsnAsnAlaGlnLeuGluPheAspAspGluProLysValIleAsnTrp
1198 GGGGATTCAGCCCTAGGAGAGAATGAACTTTGA
 400▶GlyAspSerAlaLeuGlyGluAsnGluLeu···
```

AVIAN POLYNUCLEOTIDE VACCINE FORMULA

This is a divisional application of allowed application Ser. No. 09/232,479, filed Jan. 15, 1999, now U.S. Pat. No. 6,221,362, which is a continuation-in-part of PCT/FR97/01326 filed Jul. 16, 1997 having an international filing date of Jul. 15, 1997, and designating the U.S. and claiming priority from French Application No. 96/09339, filed Jul. 19, 1996. Reference is also made to the applications of Audonnet et al., Ser. Nos. 09/232,278, 09/232,468, 09/232,477, 09/232,279, and 09/232,478 and to the application of Rijsewijk et al. Ser. No. 09/232,469, all filed Jan. 15, 1999. All of the above-mentioned applications, as well as all documents cited herein and documents referenced or cited in documents cited herein, are hereby incorporated herein by reference. Vectors of vaccines or immunological compositions of the aforementioned applications, as well as of documents cited herein or documents referenced or cited in documents cited herein or portions of such vectors (e.g., one or more or all of regulatory sequences such as DNA for promoter, leader for secretion, terminator), may to the extent practicable with respect to the preffered host of this application, also be employed in the practice of this invention; and, DNA for vectors of vaccines or immunological compositions herein can be obtained from available sources and knowledge in the art, e.g., GeneBank, such that from this disclosure, no undue experimentation is required to make or use such vectors.

The present invention relates to a vaccine formula allowing the vaccination of avian species, in particular chickens. It also relates to a corresponding method of vaccination.

Associations of vaccines against a number of viruses responsible for pathologies in chicken have already been proposed in the past.

The associations developed so far were prepared from inactivated vaccines or live vaccines. Their use poses problems of compatibility between valencies and of stability. It is indeed necessary to ensure both the compatibility between the different vaccine valencies, whether from the point of view of the different antigens used from the point of view of the formulations themselves. The problem of the conservation of such combined vaccines and also of their safety especially in the presence of an adjuvant also exists. These vaccines are in general quite expensive.

Patent applications WO-A-90 11092, WO-A-92 19183, WO-A-94 21797 and WO-A-95 20660 have made use of the recently developed technique of polynucleotide vaccines. It is known that these vaccines use a plasmid capable of expressing, in the host cells, the antigen inserted into the plasmid. All the routes of administration have been proposed (intraperitoneal, intravenous, intramuscular, transcutaneous, intradermal, mucosal and the like). Various vaccination means can also be used, such as DNA deposited at the surface of gold particles and projected so as to penetrate into the animal's skin (Tang et al., Nature, 356, 152–154, 1992) and liquid jet injectors which make it possible to transfect at the same time the skin, the muscle, the fatty tissues and the mammary tissues (Furth et al., Analytical Biochemistry, 205, 365–368, 1992). (See also U.S. Pat. Nos. 5,846,946, 5,620,896, 5,643,578, 5,580,589, 5,589,466, 5,693,622, and 5,703,055; Science, 259:1745–49, 1993; Robinson et al., seminars in IMMUNOLOGY, 9:271–83, 1997; Luke et al., J. Infect. Dis. 175(1):91–97, 1997; Norman et al., Vaccine, 15(8):801–803, 1997; Bourne et al., The Journal of Infectious Disease, 173:800–7, 1996; and, note that generally a plasmid for a vaccine or immunological composition can comprise DNA encoding an antigen operatively linked to regulatory sequences which control expression or expression and secretion of the antigen from a host cell, e.g., a mammalian cell; for instance, from upstream to downstream, DNA for a promoter, DNA for a eukaryotic leader peptide for secretion, DNA for the antigen, and DNA encoding a terminator.).

The polynucleotide vaccines may also use both naked DNAs and DNAs formulated, for example, inside lipids or cationic liposomes.

The invention therefore proposes to provide a multivalent vaccine formula which makes it possible to ensure vaccination against a number of pathogenic avian viruses.

Another objective of the invention is to provide such a vaccine formula combining different valencies while exhibiting all the criteria required for mutual compatibility and stability of the valencies.

Another objective of the invention is to provide such a vaccine formula which makes it possible to combine different valencies in the same vehicle.

Another objective of the invention is to provide such a vaccine which is easy and inexpensive to use.

Yet another objective of the invention is to provide a method for vaccinating Gallinaceans which makes it possible to obtain protection, including multivalent protection, with a high level of efficiency and of long duration, as well as good safety and an absence of residues.

The subject of the present invention is therefore an avian vaccine formula comprising at least three polynucleotide vaccine valencies each comprising a plasmid integrating, so as to express it in vivo in the host cells, a gene with one avian pathogen valency, these valencies being selected from the group consisting of Marek's disease virus (MDV), Newcastle's disease virus (NDV), infectious bursal disease virus (IBDV), infectious bronchitis virus (IBV), infectious anaemia virus (CAV), infectious laryngotracheitis virus (ILTV), encephalomyelitis virus (AEV or avian leukosis virus ALV), pneumovirosis virus, and avian plague virus, the plasmids comprising, for each valency, one or more of the genes selected from the group consisting of gB and gD for the Marek's disease virus, HN and F for the Newcastle disease virus, VP2 for the infectious bursal disease virus, S, M and N for the infectious bronchitis virus, C+NS1 for the infectious anaemia virus, gB and gD for the infectious laryngotracheitis virus, env and gag/pro for the encephalomyelitis virus, F and G for the pneumovirosis virus and HA, N and NP for the avian plague virus.

Valency in the present invention is understood to mean at least one antigen providing protection against the virus for the pathogen considered, it being possible for the valency to contain, as subvalency, one or more natural or modified genes from one or more strains of the pathogen considered.

Pathogenic agent gene is understood to mean not only the complete gene but also the various nucleotide sequences, including fragments which retain the capacity to induce a protective response. The notion of a gene covers the nucleotide sequences equivalent to those described precisely in the examples, that is to say the sequences which are different but which encode the same protein. It also covers the nucleotide sequences of other strains of the pathogen considered, which provide cross-protection or a protection specific for a strain or for a strain group. It also covers the nucleotide sequences which have been modified in order to facilitate the in vivo expression by the host animal but encoding the same protein.

Preferably, the vaccine formula according to the invention comprises three valencies chosen from Marek, infectious bursal, infectious anaemia and Newcastle. The infectious bronchitis valency can also preferably be added thereto.

On this basis of 3, 4 or 5 valencies, it will be possible to add one or more of the avian plague, laryngotracheitis, pneumovirosis and encephalomyelitis valencies.

As regards the Marek valency, two genes may be used encoding gB and gD, in different plasmids or in one and the same plasmid. The use of the gB gene alone is however preferred.

For the Newcastle valency, the two HN and F chains, integrated into two different plasmids or into one and the same plasmid, are preferably used.

For the infectious bronchitis valency, the use of the S gene is preferred. Optionally, but less preferably, S and M can be associated in a single plasmid or in different plasmids.

For the infectious anaemia valency, the two C and NS1 genes are preferably associated in the same plasmid.

For the infectious laryngotracheitis valency, the use of the gB gene alone is preferred. Optionally, but less preferably, the two gB and gD genes can be associated in different plasmids or in one and the same plasmid.

For the pneumovirosis valency, the use of the two F and G genes, in a single plasmid or in different plasmids, is preferred For the avian plague valency, the use of the HA gene is preferred. Optionally, but less preferably, it is possible to use the associations HA and NP or HA and N in different plasmids or in one and the same plasmid. Preferably, the HA sequences from more than one influenza virus strain, in particular from the different strains found in the field, are preferably associated in the same vaccine. On the other hand, NP provides cross-protection and the sequence from a single virus strain will therefore be satisfactory.

For the encephalomyelitis valency, the use of env is preferred.

The vaccine formula according to the invention can be presented in a dose volume of between 0.1 and 1 ml and in particular between 0.3 and 0.5 ml.

The dose will be generally between 10 ng and 1 mg, preferably between 100 ng and 800 μg and preferably between 0.1 μg and 50 μg per plasmid type.

Use will be preferably made of naked plasmids, simply placed in the vaccination vehicle which will be in general physiological saline and the like. It is of course possible to use all the polynucleotide vaccine forms described in the prior art and in particular formulated in liposomes.

Each plasmid comprises a promoter capable of ensuring the expression of the gene inserted, under its control, into the host cells. This will be in general a strong eukaryotic promoter and in particular a cytomegalovirus early CMV-IE promoter of human or murine origin, or optionally of another origin such as rats, pigs and guinea pigs.

More generally, the promoter may be either of viral origin or of cellular origin. As viral promoter other than CMV-IE, there may be mentioned the SV40 virus early or late promoter or the Rous sarcoma virus LTR promoter. It may also be a promoter from the virus from which the gene is derived, for example the gene's own promoter.

As cellular promoter, there may be mentioned the promoter of a cytoskeleton gene, such as, for example, the desmin promoter (Bolmont et al., Journal of Submicroscopic Cytology and Pathology, 1990, 22, 117–122; and Zhenlin et al., Gene, 1989, 78, 243–254), or alternatively the actin promoter.

When several genes are present in the same plasmid, these may be presented in the same transcription unit or in two different units.

The combination of the different vaccine valencies according to the invention may be preferably achieved by mixing the polynucleotide plasmids expressing the antigen(s) of each valency, but it is also possible to envisage causing antigens of several valencies to be expressed by the same plasmid.

The subject of the invention is also monovalent vaccine formulae comprising one or more plasmids encoding one or more genes from one of the viruses above, the genes being those described above. Besides their monovalent character, these formulae may possess the characteristics stated above as regards the choice of the genes, their combinations, the composition of the plasmids, the dose volumes, the doses and the like.

The monovalent vaccine formulae may also be used (i) for the preparation of a polyvalent vaccine formula as described above, (ii) individually against the actual pathology, (iii) associated with a vaccine of another type (live or inactivated whole, recombinant, subunit) against another pathology, or (iv) as booster for a vaccine as described below.

The subject of the present invention is in fact also the use of one or more plasmids according to the invention for the manufacture of an avian vaccine intended to vaccinate animals first vaccinated by means of a first conventional vaccine (monovalent or multivalent) of the type in the prior art, in particular selected from the group consisting of a live whole vaccine, an inactivated whole vaccine, a subunit vaccine, a recombinant vaccine, this first vaccine having (that is to say containing or capable of expressing) the antigen(s) encoded by the plasmids or antigen(s) providing cross-protection.

Remarkably, the polynucleotide vaccine has a potent booster effect which results in an amplification of the immune response and the acquisition of a long-lasting immunity.

In general, the first-vaccination vaccines can be selected from commercial vaccines available from various veterinary vaccine producers.

The subject of the invention is also a vaccination kit grouping together a vaccine formula according to the invention and a first-vaccination vaccine as described above. It also relates to a vaccine formula according to the invention accompanied by a leaflet indicating the use of this formula as a booster for a first vaccination as described above.

The subject of the present invention is also a method of avian vaccination, comprising the administration of an effective vaccine formula as described above. This vaccination method comprises the administration of one or more doses of the vaccine formula, it being possible for these doses to be administered in succession over a short period of time and/or in succession at widely spaced intervals.

The vaccine formulae according to the invention can be administered in the context of this method of vaccination, by the different routes of administration proposed in the prior art for polynucleotide vaccination and by means of known techniques of administration.

The intramuscular route, the in ovo route, the intraocular route, nebulization and drinking water will be targeted in particular.

The efficiency of presentation of the antigens to the immune system varies according to the tissues. In particular, the mucous membranes of the respiratory tree serve as barrier to the entry of pathogens and are associated with lymphoid tissues which support local immunity. In addition, the administration of a vaccine by contact with the mucous membranes, in particular the buccal mucous membrane, the pharyngeal mucous membrane and the mucous membrane of the bronchial region, is certainly of interest for mass vaccination.

Consequently, the mucosal routes of administration form part of a preferred mode of administration for the invention, using in particular neubilization or spray or drinking water. It will be possible to apply the vaccine formulae and the vaccination methods according to the invention in this context.

The subject of the invention is also the method of vaccination consisting in making a first vaccination as described above and a booster with a vaccine formula according to the invention.

In a preferred embodiment of the process according to the invention, there is administered in a first instance, to the animal, an effective dose of the vaccine of the conventional, especially inactivated, live, attenuated or recombinant, type, or alternatively a subunit vaccine so as to provide a first vaccination, and, after a period preferably of 2 to 6 weeks, the polyvalent or monovalent vaccine according to the invention is administered.

The invention also relates to the method of preparing the vaccine formulae, namely the preparation of the valencies and mixtures thereof, as evident from this description.

The invention will now be described in greater detail with the aid of the embodiments of the invention taken with reference to the accompanying drawings.

BRIEF DESCRIPTIONS OF THE DRAWINGS

FIG. No. 1: Plasmid pVR1012
FIG. No. 2: Plasmid pAB045
FIG. No. 3: Plasmid pAB080
FIG. No. 4: 4a: Sequence of the NDV HN gene, Texas GB strain
   4b: continuation of sequence of the NDV HN gene, Texan GB strain
FIG. No. 5: Plasmid pAB046
FIG. No. 6: Sequence of the NDV F gene, Texas GB strain
FIG. No. 7: Plasmid pAB047
FIG. No. 8: Sequence of the IBDV VP2 gene, Faragher strain
FIG. No. 9: Plasmid pAB048
FIG. No. 10: 10a: Sequence of the IBV S gene, Massachusetts 41 strain
   10b: Continuation of sequence of the IBV S gene, Massachusetts 41 strain
FIG. No. 11: Plasmid pAB049
FIG. No. 12: Sequence of the IBV M gene, Massachusetts 41 strain
FIG. No. 13: Plasmid pAB050
FIG. No. 14: Sequence of the IBV N gene, Massachusetts 41 strain
FIG. No. 15: Plasmid pAB051
FIG. No. 16: Plasmid pAB054
FIG. No. 17: Plasmid pAB055
FIG. No. 18: Plasmid pAB076
FIG. No. 19: Plasmid pAB089
FIG. No. 20: Plasmid pAB086
FIG. No. 21: Plasmid pAB081
FIG. No. 22: Plasmid pAB082
FIG. No. 23: Plasmid pAB077
FIG. No. 24: Plasmid pAB078
FIG. No. 25: Plasmid pAB088
FIG. No. 26: Plasmid pAB079
Sequence Listing SEQ ID No.

SEQ ID No. 1: Oligonucleotide AB062
SEQ ID No. 2: Oligonucleotide AB063
SEQ ID No. 3: Oligonucleotide AB148
SEQ ID No. 4: Oligonucleotide AB149
SEQ ID No. 5: Oligonucleotide AB072
SEQ ID No. 6: Oligonucleotide AB073
SEQ ID No. 7: Sequence of the NDV HN gene, Texas GB strain
SEQ ID No. 8: Oligonucleotide AB091
SEQ ID No. 9: Oligonucleotide AB092
SEQ ID No. 10: Sequence of the NDV F gene, Texas GB strain
SEQ ID No. 11: Oligonucleotide AB093
SEQ ID No. 12: Oligonucleotide AB094
SEQ ID No. 13: Sequence of the IBDV VP2 "gene", Faragher strain
SEQ ID No. 14: Oligonucleotide AB095
SEQ ID No. 15: Oligonucleotide AB096
SEQ ID No. 16: Sequence of the IBV S gene, Massachusetts 41 strain
SEQ ID No. 17: Oligonucleotide AB097
SEQ ID No. 18: Oligonucleotide AB098
SEQ ID No. 19: Sequence of the IBV M gene, Massachusetts 41 strain
SEQ ID No. 20: Oligonucleotide AB099
SEQ ID No. 21: Oligonucleotide AB100
SEQ ID No. 22: Sequence of the IBV N gene, Massachusetts 41 strain
SEQ ID No. 23: Oligonucleotide CD064
SEQ ID No. 24: Oligonucleotide CD065
SEQ ID No. 25: Oligonucleotide CD066
SEQ ID No. 26: Oligonucleotide AB105
SEQ ID No. 27: Oligonucleotide AB140
SEQ ID No. 28: Oligonucleotide AB141
SEQ ID No. 29: Oligonucleotide AB164
SEQ ID No. 30: Oligonucleotide AB165
SEQ ID No. 31: Oligonucleotide AB160
SEQ ID No. 32: Oligonucleotide AB161
SEQ ID No. 33: Oligonucleotide AB150
SEQ ID No. 34: Oligonucleotide AB151
SEQ ID No. 35: Oligonucleotide AB152
SEQ ID No. 36: Oligonucleotide AB153
SEQ ID No. 37: Oligonucleotide AB142
SEQ ID No. 38: Oligonucleotide AB143
SEQ ID No. 39: Oligonucleotide AB144
SEQ ID No. 40: Oligonucleotide AB145
SEQ ID No. 41: Oligonucleotide AB156
SEQ ID No. 42: Oligonucleotide AB158
SEQ ID No. 43: Oligonucleotide AB146
SEQ ID No. 44: Oligonucleotide AB147

EXAMPLES

EXAMPLE 1

Culture of the Viruses

The viruses are cultured on the appropriate cellular system until a cytopathic effect is obtained. The cellular systems to be used for each virus are well known to persons skilled in the art. Briefly, the cells sensitive to the virus used, which are cultured in Eagle's minimum essential medium (MEM medium) or another appropriate medium, are inoculated with the viral strain studied using a multiplicity of infection of 1. The infected cells are then incubated at 37° C. for the time necessary for the appearance of a complete cytopathic effect (on average 36 hours).

EXAMPLE 2

Extraction of the Viral Genomic DNAs

After culturing, the supernatant and the lysed cells are harvested and the entire viral suspension is centrifuged at 1000 g for 10 minutes at +4° C. so as to remove the cellular debris. The viral particles are then harvested by ultracentrifugation at 400,000 g for 1 hour at +4° C. The pellet is taken up in a minimum volume of buffer (10 mM Tris, 1 mM EDTA). This concentrated viral suspension is treated with proteinase K (100 µg/ml final) in the presence of sodium dodecyl sulphate (SDS) (0.5% final) for 2 hours at 37° C. The viral DNA is then extracted with a phenol/chloroform mixture and then precipitated with 2 volumes of absolute ethanol. After leaving overnight at −20° C., the DNA is centrifuged at 10,000 g for 15 minutes at +4° C. The DNA pellet is dried and then taken up in a minimum volume of sterile ultrapure water. It can then be digested with restriction enzymes.

EXAMPLE 3

Isolation of the Viral Genomic RNAs

The RNA viruses were purified according to techniques well known to persons skilled in the art. The genomic viral RNA of each virus was then isolated using the "guanidium thiocyanate/phenolchloroform" extraction technique described by P. Chromczynski and N. Sacchi (Anal. Biochem., 1987. 162, 156–159).

EXAMPLE 4

Molecular Biology Techniques

All the constructions of plasmids were carried out using the standard molecular biology techniques described by J. Sambrook et al. (*Molecular Cloning: A Laboratoxy Manual*, 2nd Edition, Cold Spring Harbor Laboratory, Cold Spring Harbor, N.Y., 1989). All the restriction fragments used for the present invention were isolated using the "Geneclean" kit (BIO 101 Inc. La Jolla, Calif.).

EXAMPLE 5

RT-PCR Technique

Specific oligonucleotides (comprising restriction sites at their 5' ends to facilitate the cloning of the amplified fragments) were synthesized such that they completely cover the coding regions of the genes which are to be amplified (see specific examples). The reverse transcription (RT) reaction and the polymerase chain reaction (PCR) were carried out according to standard techniques (Sambrook J. et al., 1989). Each RT-PCR reaction was performed with a pair of specific amplimers and taking, as template, the viral genomic RNA extracted. The complementary DNA amplified was extracted with phenol/chloroform/isoamyl alcohol (25:24:1) before being digested with restriction enzymes.

EXAMPLE 6

Plasmid pVR1012

The plasmid pVR1012 (FIG. No. 1) was obtained from Vical Inc., San Diego, Calif., USA. Its construction has been described in J. Hartikka et al. (Human Gene Therapy, 1996, 7, 1205–1217).

EXAMPLE 7

Construction of the Plasmid pAB045 (MDV gB Gene)

A PCR reaction was carried out with the Marek's disease virus (MDV) (RB1B strain) (L. Ross et al., J. Gen. Virol., 1989, 70, 1789–1804) genomic DNA, prepared according to the technique in Example 2, and with the following oligonucleotides:
AB062 (37 mer) (SEQ ID No. 1)
5' AAAACTGCAGACTATGCACTATTTTAG-GCGGAATTGC 3'
AB063 (35 mer) (SEQ ID No. 2)
5' GGAAGATCTTTACACAGCAT-CATCTTTCTGAGTCTG 3'
so as to isolate the gene encoding the gB glycoprotein from the MDV virus in the form of a PstI-BglII fragment. After purification, the 2613 bp PCR product was digested with PstI and BglI in order to isolate a 2602 bp PstI-BglII fragment. This fragment was ligated with the vector pVR1012 (Example 6), previously digested with PstI and BglII, to give the plasmid pAB045 (7455 bp) (FIG. No. 2).

EXAMPLE 8

Construction of the Plasmid pAB080 (MDV gD Gene)

A PCR reaction was carried out with the Marek's disease virus (MDV) (RB1B strain) (L. Ross et al., J. Gen. Virol., 1989, 72, 949–954) genomic DNA, prepared according to the technique in Example 2, and with the following oligonucleotides:
AB148 (29 mer) (SEQ ID No. 3)
5' AAACTGCAGATGAAAGTATTTTTTTTAG 3'
AB149 (32 mer) (SEQ ID No. 4)
5' GGAAGATCTTTATAGGCGGGAATATGCCCGTC 3'
so as to isolate the gene encoding the gD glycoprotein from the MDV virus in the form of a PstI-BglII fragment. After purification, the 1215 bp PCR product was digested with PstI and BglII in order to isolate a 1199 bp PstI-BglII fragment. This fragment was ligated with the vector pVR1012 (Example 6), previously digested with PstI and BglII, to give the plasmid pAB080 (6051 bp) (FIG. No. 3).

EXAMPLE 9

Construction of the Plasmid pAB046 (NDV HN Gene)

An RT-PCR reaction according to the technique of Example 5 was carried out with the Newcastle disease virus (NDV) (Texas GB strain) genomic RNA, prepared according to the technique of Example 3, and with the following oligonucleotides:
AB072 (39 mer) (SEQ ID No. 5)
5' AGAATGCGGCCGCGATGGGCTCCA-GATCTTCTACCAG 3'
AB094 (34 mer) (SEQ ID No. 6)
5' CGCGGATCCTTAAATCCCATCATCCTTGAGAATC 3'
so as to isolate the gene encoding the HN glycoprotein from the NDV virus, Texas GB strain (FIG. No. 4 and SEQ ID No. 7) in the form of an NotI-BamHI fragment. After purification, the 1741 bp RT-PCR product was digested with NotI and BamHI in order to isolate a 1723 bp NotI-BamHI fragment. This fragment was ligated with the vector pVR1012 (Example 6), previously digested with NotI and BamHI, to give the plasmid pAB046 (6616 bp) (FIG. No. 5).

EXAMPLE 10

Construction of the Plasmid pAB047 (NDV F Gene)

An RT-PCR reaction according to the technique of Example 5 was carried out with the Newcastle disease virus (NDV) (Texas GB strain) genomic RNA, prepared according to the technique of Example 3, and with the following oligonucleotides:
AB091 (37 mer) (SEQ ID No. 8)
5' AGAATGCGGCCGCGATGGGCTCCA-GATCTTCTACCAG 3'
AB092 (34 mer) (SEQ ID No. 9)
5' TGCTCTAGATCATATTTTTGTAGTGGCTCTCATC 3'
so as to isolate the gene encoding the F glycoprotein from the NDV virus, Texas GB strain (FIG. No. 6 and SEQ ID No. 10) in the form of an NotI-XbaI fragment. After purification, the 1684 bp RT-PCR product was digested with NotI and XbaI in order to isolate a 1669 bp NotI-XbaI fragment. This fragment was ligated with the vector pVR1012 (Example 6), previously digested with NotI and XbaI, to give the plasmid pAB047 (6578 bp) (FIG. No. 7).

EXAMPLE 11

Construction of the Plasmid pAB048 (IBDV VP2 Gene)

An RT-PCR reaction according to the technique of Example 5 was carried out with the infectious bursal disease virus (IBDV) (Faragher strain) genomic RNA, prepared according to the technique of Example 3, and with the following oligonucleotides:
AB093 (33 mer) (SEQ ID No. 11)
5' TCAGATATCGATGACAAACCTGCAAGATCAAAC 3'
AB094 (38 mer) (SEQ ID No. 12)
5' AGAATGCGGCCGCTTACCTCCTTATAGC-CCGGATTATG 3'
so as to isolate the sequence encoding the VP2 protein from the IBDV virus, Faragher strain (FIG. No. 8 and SEQ ID No. 13) in the form of an EcoRV-NotI fragment. After purification, the 1384 bp RT-PCR product was digested with EcoRV and NotI in order to isolate a 1367 bp EcoRV-NotI fragment. This fragment was ligated with the vector pVR1012 (Example 6), previously digested with EcoRV and NotI, to give the plasmid pAB048 (6278 bp) (FIG. No. 9).

EXAMPLE 12

Construction of the plasmid pAB049 (IBV S1 Gene)

An RT-PCR reaction according to the technique of Example 5 was carried out with the chicken infectious bronchitis virus (IPV) (Massachusetts 41 strain) genomic RNA, prepared according to the technique of Example 3, and with the following oligonucleotides:
AB095 (32 mer) (SEQ ID No. 14)
5' ACGCGTCGACATGTTGGTAACACCTCTTTTAC 3'
AB096 (35 mer) (SEQ ID No. 15)
5' GGAAGATCTTCATTAACGTCTAAAAC-GACGTGTTC 3'
so as to isolate the sequence encoding the S1 subunit of the S glycoprotein from the IBV virus, Massachusetts 41 strain (FIG. No. 10 and SEQ ID No. 16) in the form of a SalI-BglII fragment. After purification, the 1635 bp RT-PCR product was digested with SalI and BglII in order to isolate a 1622 bp SalI-BglII fragment. This fragment was ligated with the vector pVR1012 (Example 6), previously digested with SalLI and BglII, to give the plasmid pAB049 (6485 bp) (FIG. No. 11).

EXAMPLE 13

Construction of the Plasmid pAB050 (IBV M Gene)

An RT-PCR reaction according to the technique of Example 5 was carried out with the chicken infectious bronchitis virus (IBV) (Massachusetts 41 strain) genomic RNA, prepared according to the technique of Example 3, and with the following oligonucleotides:
AB097 (37 mer) (SEQ ID No. 17)
5' ATAAGAATGCGGCCGCATGTCCAAC-GAGACAAATTGTAC 3'
AB098 (38 mer) (SEQ ID No. 18)
5' ATAAGAATGCGGCCGCTTTAGGTGTAAA-GACTACTCCC 3'
so as to isolate the gene encoding the M glycoprotein from the IBV virus, Massachusetts 41 strain (FIG. No. 12 and SEQ ID No. 19) in the form of a NotI-NotI fragment. After purification, the 710 bp RT-PCR product was digested with NotI in order to isolate a 686 bp NotI-NotI fragment. This fragment was ligated with the vector pVR1012 (Example 6), previously digested with NotI, to give the plasmid pAB050 (5602 bp) which contains the IBV M gene in the correct orientation relative to the promoter (FIG. No. 13).

EXAMPLE 14

Construction of the Plasmid pAB051 (IBV N Gene)

An RT-PCR reaction according to the technique of Example 5 was carried out with the chicken infectious bronchitis virus (IBV) (Massachusetts 41 strain) genomic RNA, prepared according to the technique of Example 3, and with the following oligonucleotides:
AB099 (34 mer) (SEQ ID No. 20)
5' AAAACTGCAGTCATGGCAAGCGGTAAG-GCAACTG 3'
AB100 (33 mer) (SEQ ID No. 21)
5' CGCGGATCCTCAAAGTTCATTCTCTCCTAGGGC 3'
so as to isolate the gene encoding the N protein from the IBV virus, Massachusetts 41 strain (FIG. No. 14 and SEQ ID No. 22) in the form of a PstI-BamHI fragment. After purification, the 1250 bp RT-PCR product was digested with PstI and BamHI in order to isolate a 1233 bp PstI-BamHI fragment. This fragment was ligated with the vector pVR1012 (Example 6), previously digested with PstI and BamHI, to give the plasmid pAB051 (6092 bp) (FIG. No. 15).

EXAMPLE 15

Construction of the Plasmid pAB054 (VAC VP1 Gene)

A PCR reaction was carried out with the chicken anaemia virus (CAV) (Cuxhaven-1 strain) genomic DNA (B. Meehan et al., Arch. Virol., 1992, 124, 301–319), prepared according to the technique of Example 2, and with the following oligonucleotides:
CD064 (39 mer) (SEQ ID No. 23)

5' TTCTTGCGGCCGCCATGGCAAGAC-GAGCTCGCAGACCGA 3'
CD065 (38 mer) (SEQ ID No. 24)
5' TTCTTGCGGCCGCTCAGGGCTGCGTC-CCCCAGTACATG 3'
so as to isolate the gene encoding the CAV VP1 capsid protein in the form of an NotI-NotI fragment. After purification, the 1377 bp PCR product was digested with NotI in order to isolate a 1359 bp NotI-NotI fragment. This fragment was ligated with the vector pVR1012 (Example 6), previously digested with NotI, to give the plasmid pAB054 (6274 bp) which contains the CAV VP1 gene in the correct orientation relative to the promoter (FIG. No. 16).

EXAMPLE 16

Construction of the Plasmid pAB055 (CAV VP2 Gene)

A PCR reaction was carried out with the chicken anaemia virus (CAV) (Cuxhaven-1 strain) genomic DNA (B. Meehan et al., Arch. Virol., 1992, 124, 301–319), prepared according to the technique of Example 2, and with the following oligonucleotides:
CD066 (39 mer) (SEQ ID No. 25)
5' TTCTTGCGGCCGCCATGCACGGGAACG-GCGGACAACCGG 3'
AB105 (32 mer) (SEQ ID No. 26)
5' CGCGGATCCTCACACTATACGTACCGGGGCGG 3'
so as to isolate the gene encoding the CAV virus VP2 protein in the form of an NotI-BamHI fragment. After purification, the 674 bp PCR product was digested with NotI and BamHI in order to isolate a 659 bp NotI-BamHI fragment. This fragment was ligated with the vector pVR1012 (Example 6), previously digested with NotI and BamHI, to give the plasmid pAB055 (5551 bp) (FIG. No. 17).

EXAMPLE 17

Construction of the Plasmid pAB076 (ILTV gB Gene)

A PCR reaction was carried out with the chicken infectious laryngotracheitis virus (ILTV) (SA-2 strain) genomic DNA (K. Kongsuwan et al., Virology, 1991, 184, 404–410), prepared according to the technique of Example 2, and with the following oligonucleotides:
AB140 (38 mer) (SEQ ID No. 27)
5' TTCTTGCGGCCGCATGTCTTGAAAATGCTGATC 3'
AB141 (36 mer) (SEQ ID No. 28)
5' TTCTTGCGGCCGCTTATTCGTCT-TCGCTTTCTTCTG 3'
so as to isolate the gene encoding the ILTV virus gB glycoprotein in the form of an NotI-NotI fragment. After purification, the 2649 bp PCR product was digested with NotI in order to isolate a 2631 bp NotI-NotI fragment. This fragment was ligated with the vector pVR1012 (Example 6), previously digested with NotI, to give the plasmid pAB076 (7546 bp) which contains the ILTV gB gene in the correct orientation relative to the promoter (FIG. No. 18).

EXAMPLE 18

Construction of the Plasmid pAB089 (ILTV gD Gene)

A PCR reaction was carried out with the chicken infectious laryngotracheitis virus (ILTV) (SA-2 strain) genomic DNA (M. Johnson et al., 1994, Genbank sequence accession No. =L31965), prepared according to the technique of Example 2, and with the following oligonucleotides:
AB164 (33 mer) (SEQ ID No. 29)
5' CCGGTCGACATGGACCGCCATTTATTTTTGAGG 3'
AB165 (33 mer) (SEQ ID No. 30)
5' GGAAGATCTTTACGATGCTCCAAACCAGTAGCC 3'
so as to isolate the gene encoding the ILTV virus gD glycoprotein in the form of an SalI-BglII fragment. After purification, the 1134 bp PCR product was digested with SalI and BglII in order to isolate a 1122 bp SalI-BglII fragment. This fragment was ligated with the vector pVR1012 (Example 6), previously digested with SalI-BglII, to give the plasmid pAB089 (5984 bp) (FIG. No. 19).

EXAMPLE 19

Construction of the Plasmid pAB086 (AEV env Gene)

An RT-PCR reaction according to the technique of Example 5 was carried out with the avian encephalomyelitis virus (AEV) (Type C) genomic RNA (E. Bieth et al., Nucleic Acids Res., 1992, 20, 367), prepared according to the technique of Example 3, and with the following oligonucleotides:
AB160 (54 mer) (SEQ ID No. 31)
5' TTTGATATCATGGAAGCCGTCATTAAG-GCATTTCTGACTGGATACCCTGGGAA G3'
AB161 (31 mer) (SEQ ID No. 32)
5' TTTGGATCCTTATACTATTCTGCTTTCAGGC 3'
so as to isolate the sequence encoding the AEV virus Env glycoprotein in the form of an EcoRV-BamHI fragment. After purification, the 1836 bp RT-PCR product was digested with EcoRV and BamHI in order to isolate a 1825 bp EcoRV-BamHI fragment. This fragment was ligated with the vector pVR1012 (Example 6), previously digested with EcoRV and BamHI, to give the plasmid pAB086 (6712 bp) (FIG. No. 20).

EXAMPLE 20

Construction of the Plasmid pAB081 (AEV gag/pro Gene)

An RT-PCR reaction according to the technique of Example 5 was carried out with the avian encephalomyelitis virus (AEV) (Type C) genomic RNA (E. Bieth et al., Nucleic Acids Res., 1992, 20, 367), prepared according to the technique of Example 3, and with the following oligonucleotides:
ABS150 (31 mer) (SEQ ID No. 33)
5' ACGCGTCGACATGGAAGCCGTCATTAAGGTG 3'
AB151 (32 mer) (SEQ ID No. 34)
5' TGCTCTAGACTATAAATTTGTCAAGCGGAGCC 3'
so as to isolate the sequence encoding the AEV virus Gag and Pro proteins in the form of an SalI-XbaI fragment. After purification, the 2125 bp RT-PCR product was digested with SalI-XbaI in order to isolate a 2111 bp SalI-XbaI fragment. This fragment was ligated with the vector pVR1012 (Example 6), previously digested with SalI and XbaI, to give the plasmid pAB081 (6996 bp) (FIG. No. 21).

EXAMPLE 21

Construction of the Plasmid pAB082 (Pneumovirus G Gene)

An RT-PCR reaction according to the technique of Example 5 was carried out with the turkey rhinotracheitis virus (TRV) (2119 strain) genomic RNA (K. Juhasz et al., J. Gen. Virol., 1994, 75. 2873–2880), prepared according to the technique of Example 3, and with the following oligonucleotides:
AB152 (32 mer) (SEQ ID No. 35)
5' AAACTGCAGAGATGGGGTCAGAGCTCTACATC 3'
AB153 (31 mer) (SEQ ID No. 36)
5' CGAAGATCTTTATTGACTAGTACAGCACCAC 3'
so as to isolate the gene encoding the TRV virus G glycoprotein in the form of a PstI-BglII fragment. After purification, the 2165 bp RT-PCR product was digested with PstI and BglII in order to isolate a 1249 bp PstI-BglII fragment. This fragment was ligated with the vector pVR1012 (Example 6), previously digested with PstI and BglII, to give the plasmid pAB082 (6101 bp) (FIG. No. 22).

EXAMPLE 22

Construction of the Plasmid pAB077 (Avian Plague HA Gene, H2N2 Strain)

An RT-PCR reaction according to the technique of Example 5 was carried out with the avian plague virus (AIV) (H2N2 Postdam strain) genomic RNA (J. Schäfer et al., Virology, 1993, 194, 781–788), prepared according to the technique of Example 3, and with the following oligonucleotides:
AB142 (33 mer) (SEQ ID No. 37)
5' AAACTGCAGCAATGGCCATCATTTATCTAATTC 3'
AB143 (31 mer) (SEQ ID No. 38)
5' CGAAGATCTTCATATGCAGATTCTGCATTGC 3'
so as to isolate the gene encoding the HA glycoprotein from the avian plague virus (H2N2 strain) in the form of a PstI-BglII fragment. After purification, the 1709 bp RT-PCR product was digested with PstI and BglII in order to isolate a 1693 bp PstI-BglII fragment. This fragment was ligated with the vector pVR1012 (Example 6), previously digested with PstI and BglII, to give the plasmid pAB077 (6545 bp) (FIG. No. 23).

EXAMPLE 23

Construction of the Plasmid pAB078 (Avian Plague HA Gene, H7N7 Strain)

An RT-PCR reaction according to the technique of Example 5 was carried out with the avian plague virus (AIV) (H7N7 Leipzig strain) genomic RNA (C. Rohm et al., Virology, 1995, 209, 664–670), prepared according to the technique of Example 3, and with the following oligonucleotides:
AB144 (31 mer) (SEQ ID No. 39)
5' AAACTGCAGATGAACACTCAAATCCTGATAC 3'
AB145 (31 mer) (SEQ ID No. 40)
5' TTTGGATCCTTATATACAAATAGTGCACCGC 3'
so as to isolate the gene encoding the HA glycoprotein from the avian plague virus (H7N7 strain) in the form of a PstI-BamHI fragment. After purification, the 1707 bp RT-PCR product was digested with PstI and BamHI in order to isolate a 1691 bp PstI-BamHI fragment. This fragment was ligated with the vector pVR1012 (Example 6), previously digested with PstI and BamHI, to give the plasmid pAB078 (6549 bp) (FIG. No. 24).

EXAMPLE 24

Construction of the Plasmid pAB088 (Avian Plague NP Gene, H1N1 Strain)

An RT-PCR reaction according to the technique of Example 5 was carried out with the avian influenza virus (AIV) (H1N1 Bavaria strain) genomic RNA (M. Gammelin et al., Virology, 1989, 170, 71–80), prepared according to the technique of Example 3, and with the following oligonucleotides:
AB156 (32 mer) (SEQ ID No. 41)
5' CCGGTCGACATGGCGTCTCAAGGCACCAAACG 3'
AB158 (30 mer) (SEQ ID No. 42)
5' CGCGGATCCTTAATTGTCATACTCCTCTGC 3'
so as to isolate the gene encoding the avian influenza virus NP nucleoprotein in the form of a SalI-BamHI fragment. After purification, the 1515 bp RT-PCR product was digested with SalI and BamHI in order to isolate a 1503 bp SalI-BamHI fragment. This fragment was ligated with the vector pVR1012 (Example 6), previously digested with SalI and BamHI, to give the plasmid pAB088 (6371 bp) (FIG. No. 25).

EXAMPLE 25

Construction of the Plasmid pAB079 (Avian Plague N Gene, H7N1 Strain)

An RT-PCR reaction according to the technique of Example S was carried out with the avian plague virus (AIV) (H7N1 Rostock strain) genomic RNA (J. McCauley, 1990, Genbank sequence accession No.=X52226), prepared according to the technique of Example 3, and with the following oligonucleotides:
AB146 (35 mer) (SEQ ID No. 43)
5' CGCGTCGACATGAATCCAAATCAGAAAATAATAAC 3'
AB147 (31 mer) (SEQ ID No. 44)
5' GGAAGATCTCTACTTGTCAATGGTGAATGGC 3'
so as to isolate the gene encoding the N glycoprotein from the avian plague virus (H7N1 strain) in the form of an SalI-BglII fragment. After purification, the 1361 bp RT-PCR product was digested with SalI and BglII in order to isolate a 1350 bp SalI-BglII fragment. This fragment was ligated with the vector pVR1012 (Example 6), previously digested with Sal1I and BglII, to give the plasmid pAB079 (6212 bp) (FIG. No. 26).

EXAMPLE 26

Preparation and Purification of the Plasmids

For the preparation of the plasmids intended for the vaccination of animals, any technique may be used which makes it possible to obtain a suspension of purified plasmids predominantly in the supercoiled form. These techniques are well known to persons skilled in the art. There may be mentioned in particular the alkaline lysis technique followed by two successive ultracentrifugations on a caesium chloride gradient in the presence of ethidium bromide as described in J. Sambrook et al. (*Molecular Cloning: A Laboratory Manual*, 2nd edition, Cold Spring Harbor Laboratory, Cold Spring Harbor, N.Y., 1989). Reference may also be made to patent applications PCT WO 95/21250 and PCT WO 96/02658 which describe methods for producing, on an industrial scale, plasmids which can be used for vaccination. For the purposes of the manufacture of vaccines (see Example 17), the purified plasmids are resuspended so as to obtain solutions at a high concentration (>2 mg/ml) which are compatible with storage. To do this the plasmids are resuspended either in ultrapure water or in TE buffer (10 mM Tris-HCl; 1 mM EDTA, pH 8.0).

EXAMPLE 27

Manufacture of the Associated Vaccines

The various plasmids necessary for the manufacture of an associated vaccine are mixed starting with their concentrated solutions (Example 16). The mixtures are prepared such that the final concentration of each plasmid corresponds to the effective dose of each plasmid. The solutions which can be used to adjust the final concentration of the vaccine may be either a 0.9% NaCl solution, or PBS buffer.

Specific formulations such as liposomes, cationic lipids, may also be used for the manufacture of the vaccines.

EXAMPLE 28

Vaccination of Chickens

The chickens are vaccinated with doses of 10, 50 or 100 μg per plasmid. The injections can be performed with a needle by the intramuscular route. The sites of injection are the carina (for chickens more than 2 weeks old) and the thigh (for 1-day-old or older chickens). In this case, the vaccinal doses are administered in the volume of 0.1 to 0.3 ml.

In adult chickens (more than 20 weeks old) the injections are also performed by the intramuscular route using a liquid jet injection apparatus (with no needle) which has been specially designed for the vaccination of chickens (for example AVIJET apparatus). In this case, the injected volume is 0.3 ml. The injection may be performed in the carina or at the level of the thigh. Likewise, in adult chickens, the injections may be performed with a needle by the intramuscular route, in the carina or in the thigh, in a volume of 0.3 ml. The injection of the plasmid vaccines can also be done in ovo. In this case, special formulations as mentioned in Example 29 may be used. The volume injected into the 18-day embryonated egg is between 50 μl and 200 μl.

What is claimed is:

1. An avian vaccine comprising a plasmid that contains and expresses in vivo in an avian host cell a nucleic acid molecule having a sequence encoding the Newcastle disease virus HN protein, and a pharmaceutically acceptable carrier.

2. The vaccine according to claim 1, wherein expression of the sequence is under the control of a promoter selected from the group consisting of a CMV-IE promoter, a SV40 early promoter, a SV40 late promoter, a Rous sarcoma virus LTR promoter, and a promoter of a cytoskeleton gene.

3. The vaccine according to claim 1, wherein expression of the sequence is under the control of a CMV-IE promoter.

4. A method of vaccination of an avian host comprising: administering to said avian a vaccine selected from the group consisting of a live whole vaccine, an inactivated whole vaccine, a subunit vaccine, and a recombinant vaccine; and thereafter, administering to said avian a vaccine as claimed in claim 1.

5. A method of vaccination of an avian host comprising administering to said avian a vaccine as claimed in claim 1.

6. The vaccine according to claim 1, wherein the plasmid further contains and expresses in vivo in an avian host cell a nucleic acid molecule having a sequence encoding the Newcastle disease virus F protein.

7. The vaccine according to claim 6, wherein expression of the sequence(s) is under the control of a promoter selected from the group consisting of a CMV-IE promoter, a SV40 early promoter, a SV40 late promoter, a Rous sarcoma virus LTR promoter, and a promoter of a cytoskeleton gene.

8. The vaccine according to claim 6, wherein expression of the sequence(s) is under the control of a CMV-IE promoter.

9. A method of vaccination of an avian host comprising administering to said avian a vaccine as claimed in claim 6.

10. The vaccine according to claim 1, which further comprises a plasmid that contains and expresses in vivo in an avian host cell a nucleic acid molecule having a sequence encoding the Newcastle disease virus F protein.

11. The vaccine according to claim 10, wherein expression of the sequence(s) is under the control of a promoter selected from the group consisting of a CMV-IE promoter, a SV40 early promoter, a SV40 late promoter, a Rous sarcoma virus LTR promoter, and a promoter of a cytoskeleton gene.

12. The vaccine according to claim 10, wherein expression of the sequence(s) is under the control of a CMV-IE promoter.

13. A method of vaccination of an avian host comprising administering to said avian a vaccine as claimed in claim 10.

* * * * *

UNITED STATES PATENT AND TRADEMARK OFFICE
CERTIFICATE OF CORRECTION

PATENT NO. : 6,464,984 B2
DATED : October 15, 2002
INVENTOR(S) : Jean-Christophe Audonnet et al.

It is certified that error appears in the above-identified patent and that said Letters Patent is hereby corrected as shown below:

<u>Title page,</u>
Item [75], Inventors, change "Lyons" to -- Lyon --.
Item [73], Assignee, change "Lyons" to -- Lyon --.

Signed and Sealed this

Eleventh Day of February, 2003

JAMES E. ROGAN
*Director of the United States Patent and Trademark Office*

UNITED STATES PATENT AND TRADEMARK OFFICE
CERTIFICATE OF CORRECTION

PATENT NO.      : 6,464,984 B2
DATED           : October 15, 2002
INVENTOR(S)     : Jean-Christophe Audonnet et al.

It is certified that error appears in the above-identified patent and that said Letters Patent is hereby corrected as shown below:

<u>Title page,</u>
Please insert:
-- Foreign Application Priority Data
[30]    July 19, 1996   (FR)………………..96 09339 --

Signed and Sealed this

Twenty-second Day of July, 2003

JAMES E. ROGAN
*Director of the United States Patent and Trademark Office*

SEQUENCE LISTING

```
<160> NUMBER OF SEQ ID NOS: 44

<210> SEQ ID NO 1
<211> LENGTH: 37
<212> TYPE: DNA
<213> ORGANISM: Marek's disease gammaherpesvirus MKT-1

<400> SEQUENCE: 1
aaaactgcag actatgcact attttaggcg gaattgc                            37

<210> SEQ ID NO 2
<211> LENGTH: 35
<212> TYPE: DNA
<213> ORGANISM: Marek's disease gammaherpesvirus MKT-1

<400> SEQUENCE: 2
ggaagatctt tacacagcat catcttctga gtctg                              35

<210> SEQ ID NO 3
<211> LENGTH: 29
<212> TYPE: DNA
<213> ORGANISM: Marek's disease gammaherpesvirus MKT-1

<400> SEQUENCE: 3
aaactgcaga tgaaagtatt tttttttag                                     29

<210> SEQ ID NO 4
<211> LENGTH: 32
<212> TYPE: DNA
<213> ORGANISM: Marek's disease gammaherpesvirus MKT-1

<400> SEQUENCE: 4
ggaagatctt tataggcggg aatatgcccg tc                                 32

<210> SEQ ID NO 5
<211> LENGTH: 39
<212> TYPE: DNA
<213> ORGANISM: Newcastle disease virus

<400> SEQUENCE: 5
ataagaatgc ggccgccatg gaccgtgcag ttagcagag                          39

<210> SEQ ID NO 6
<211> LENGTH: 34
<212> TYPE: DNA
```

<213> ORGANISM: Newcastle disease virus

<400> SEQUENCE: 6

| cgcggatcct taaatcccat catccttgag aatc | 34 |

<210> SEQ ID NO 7
<211> LENGTH: 1716
<212> TYPE: DNA
<213> ORGANISM: Newcastle disease virus

<400> SEQUENCE: 7

| atggaccgtg cagttagcag agttgcgcta gagaatgaag aaagagaagc aaagaataca | 60 |
| tggcgctttg tattccggat tgcaatctta cttttaatag taacaacctt agccatctct | 120 |
| gcaaccgccc tggtatatag catggaggct agcacgcctg gcgaccttgt tggcataccg | 180 |
| actatgatct ctaaggcaga agaaaagatt acatctgcac tcagttctaa tcaagatgta | 240 |
| gtagatagga tatataagca ggtggccctt gagtctccat tggcgttgct aaacactgaa | 300 |
| tctgtaatta tgaatgcaat aacgtctctc tcttatcaaa tcaatggagc tgcaaataat | 360 |
| agcgggtgtg gggcacctgt tcatgaccca gattatatcg gggggatagg caaagaactt | 420 |
| attgtggatg acgctagtga tgtcacatca ttctatccct ctgcgttcca agaacacctg | 480 |
| aactttatcc cggcacctac tacaggatca ggttgcactc ggataccctc attcgacata | 540 |
| agcgctaccc actactgtta cactcacaat gtgatattat ctggttgcag agatcactca | 600 |
| cactcatatc agtacttagc acttggcgtg cttcggacat ctgcaacagg agggtattc | 660 |
| ttttctactc tgcgttccat caatttggat gacagccaaa atcggaagtc ttgcagtgtg | 720 |
| agtgcaactc ccttaggttg tgatatgctg tgctctaaaa tcacagagac tgaggaagag | 780 |
| gattatagtt caattacgcc tacatcgatg gtgcacggaa ggttagggtt tgacggtcaa | 840 |
| taccatgaga aggacttaga cgtcataact ttatttaagg attgggtggc aaattaccca | 900 |
| ggagtggggg gtgggtcttt tattaacaac cgcgtatggt tcccagtcta cggagggcta | 960 |
| aaacccaatt cgcctagtga caccgcacaa gaagggagat atgtaatata caagcgctac | 1020 |
| aatgacacat gcccagatga acaagattac cagattcgga tggctaagtc ttcatataag | 1080 |
| cctgggcggt tggtggaaaa acgcgtacag caggccatct tatctatcaa ggtgtcaaca | 1140 |
| tctttgggcg aggacccggt gctgactgta ccgcctaata caatcacact catggggcc | 1200 |
| gaacggagag ttctcacagt agggacatct catttcttgt accagcgagg tctcttcatac | 1260 |
| ttctctcctg ctttattata ccctatgaca gtcaacaaca aaacggctac tcttcatagt | 1320 |
| ccttacacat tcaatgcttt cactaggcca gtagtgtcc cttgtcaggc atcagcaaga | 1380 |
| tgccccaact catgtgtcac tggagtttat actgatccgt atcccttagt cttccatagg | 1440 |
| aaccatacct tgcgggggt attcgggaca atgcttgatg atgaacaagc aagacttaac | 1500 |
| cctgtatctg cagtatttga taacatatcc cgcagtcgca taacccgggt aagttcaagc | 1560 |
| cgtactaagg cagcatacac gacatcgaca tgttttaaag ttgtcaagac caataaaaca | 1620 |
| tattgcctca gcattgcaga aatatccaat accctcttcg gggaattcag gatcgttcct | 1680 |
| ttactagttg agattctcaa ggatgatggg atttaa | 1716 |

<210> SEQ ID NO 8
<211> LENGTH: 37
<212> TYPE: DNA
<213> ORGANISM: Newcastle disease virus

<400> SEQUENCE: 8
agaatgcggc cgcgatgggc tccagatctt ctaccag 37

<210> SEQ ID NO 9
<211> LENGTH: 34
<212> TYPE: DNA
<213> ORGANISM: Newcastle disease virus

<400> SEQUENCE: 9
tgctctagat catatttttg tagtggctct catc 34

<210> SEQ ID NO 10
<211> LENGTH: 1662
<212> TYPE: DNA
<213> ORGANISM: Newcastle disease virus

<400> SEQUENCE: 10
atgggctcca gatcttctac caggatcccg gtacctctaa tgctgatcat ccgaaccgcg 60
ctgacactga gctgtatccg tctgacaagc tctcttgatg caggcctct tgcggctgca 120
gggatcgtgg taacaggaga taaagcagtc aacatataca cctcatccca gacagggtca 180
atcatagtta agttactccc gaatatgccc aaggacaaag aggtgtgtgc aaaagcccca 240
ttggaggcat acaacaggac actgactact ttactcaccc cccttggtga ttctatccgc 300
aggatacaag agtctgtgac tacttccgga ggaaggagac agagacgctt tataggtgcc 360
attatcggca gtgtagctct tggggttgcg acagctgcac agataacagc agcttcggcc 420
ctgatacaag ccaaccagaa tgctgccaac atcctccggc ttaaagagag cattgctgca 480
accaatgaag ctgtgcacga ggtcactgac ggattatcac aactagcagt ggcagtaggg 540
aagatgcaac agtttgtcaa tgaccagttc aataatacag cgcaagaatt ggactgtata 600
aaaattgcac agcaggtcgg tgtagaactc aacttgtacc taactgaatt gactacagta 660
tttgggccac aaatcacttc ccctgcctta actcagctga ctatccaagc gctttacaat 720
ctagctggtg gtaatatgga ttacttgctg actaagttag gtgtagggaa caaccaactc 780
agctcattaa ttggtagcgg cttgatcacc ggcaacccta ttctgtacga ctcacagact 840
cagatcttgg gtatacaggt aacttttgcct tcagttggga acctgaataa tatgcgtgcc 900
acctacctgg agaccttatc tgtaagcaca accaagggat tgcctcagc acttgtccca 960
aaagtggtga cacaggtcgg ttccgtgata aagaacttg cacactcata ctgtataggg 1020
accgacttgg atttatactg tacaagaata gtgacattcc ctatgtctcc tggtatttat 1080
tcttgtctga gcggtaatac atcggcttgc atgtattcaa agactgaagg cgcacttact 1140
acgccatata tggctctcaa aggctcagtt attgccaatt gcaagctgac aacatgtaga 1200
tgtgcagatc ccccaggtat catatcgcaa aattatggag aagctgtgtc cttaatagat 1260
aggcactcat gcaacgtctt atccttagac gggataactc tgaggctcag tggggaattt 1320
gatgcaacct atcaaaagaa tatctctata ctagattctc aagttatagt gacaggcaat 1380
cttgatatat caactgagct tgggaatgtc aacaactcaa taagtaatgc cctgaataag 1440
ttagaggaaa gcaacagcaa actagacaaa gtcaatgtca aactgaccag cacatctgct 1500
ctcattacct acatcgtttt aactgtcata tctcttgttt ttggtgtact tagcctggtt 1560
ctagcatgct acctgatgta caagcaaaag gcacaacaaa agaccttgtt atggcttggg 1620
aataataccc ttgatcagat gagagccact acaaaaatat ga 1662

<210> SEQ ID NO 11

<210> SEQ ID NO 11
<211> LENGTH: 33
<212> TYPE: DNA
<213> ORGANISM: Infectious bursal disease virus

<400> SEQUENCE: 11
tcagatatcg atgacaaacc tgcaagatca aac                              33

<210> SEQ ID NO 12
<211> LENGTH: 38
<212> TYPE: DNA
<213> ORGANISM: Infectious bursal disease virus

<400> SEQUENCE: 12
agaatgcggc cgcttacctc cttatagccc ggattatg                         38

<210> SEQ ID NO 13
<211> LENGTH: 1362
<212> TYPE: DNA
<213> ORGANISM: Infectious bursal disease virus

<400> SEQUENCE: 13
atgacaaacc tgcaagatca aacccaacag attgttccgt tcatacggag ccttctgatg      60
ccaacaaccg gaccggcgtc cattccggac gacaccctgg agaagcacac tctcaggtca     120
gagacctcga cctacaattt gactgtgggg acacagggt cagggctaat tgtctttttc     180
cctggattcc ctggctcaat tgtgggtgct cactacacac tgcagagcaa tgggaactac     240
aagttcgatc agatgctcct gactgccag acctacggg ccagctacaa ctactgcaga     300
ctagtgagtc ggagtctcac agtgaggtca agcacactcc ctggtggcgt ttatgcacta     360
aacggcacca taaacgccgt gaccttccaa ggaagcctga gtgaactgac agatgttagc     420
tacaatgggt tgatgtctgc aacagccaac atcaacgaca aaattgggaa tgtcctggta     480
ggggaagggg tcactgtcct cagcctaccc acatcatatg atcttgggta tgtgaggctt     540
ggtgacccca ttcccgctat agggcttgac ccaaaaatgg tagctacatg cgacagcagt     600
gacaggccca gagtctacac cataactgca gccgatgatt accaattctc atcacagtac     660
caaccaggtg gggtaacaat cacactgttc tcagccaaca ttgatgctat cacaagcctc     720
agcattgggg gagagctcgt gtttcaaaca agcgtccaag gccttgtact gggcgccacc     780
atctacctta taggctttga tgggactgcg gtaatcacca gagctgtagc cgcagataat     840
gggctgacgg ccggcaccga caatcttatg ccattcaatc ttgtcattcc aaccaatgag     900
ataacccagc caatcacatc catcaaactg gagatagtga cctccaaaag tggtggtcag     960 gcagggatc agatgtcatg gtcggcaagt gggagcctag cagtgacgat ccatggtggc    1020
aactatccag ggcccctccg tcccgtcaca ctagtagcct acgaaagagt ggcaacagga    1080
tccgtcgtta cggtcgctgg ggtgagtaac ttcgagctga ttccaaatcc tgaactagca    1140
aagaacctgg ttacagaata cggccgattt gacccaggag ccatgaacta cacaaaattg    1200
atactgagtg agagggaccg tcttggcatc aagaccgtct ggccaacaag ggagtacact    1260
gattttcgtg agtacttcat ggaggtggcc gacctcaact ctcccctgaa gattgcagga    1320
gcatttggct tcaaagacat aatccgggct ataaggaggt aa                     1362

<210> SEQ ID NO 14
<211> LENGTH: 32
<212> TYPE: DNA
<213> ORGANISM: chicken infectious bronchitis virus

<400> SEQUENCE: 14

```
acgcgtcgac atgttggtaa cacctctttt ac                                    32

<210> SEQ ID NO 15
<211> LENGTH: 35
<212> TYPE: DNA
<213> ORGANISM: chicken infectious bronchitis virus

<400> SEQUENCE: 15
ggaagatctt cattaacgtc taaaacgacg tgttc                                 35

<210> SEQ ID NO 16
<211> LENGTH: 1614
<212> TYPE: DNA
<213> ORGANISM: chicken infectious bronchitis virus

<400> SEQUENCE: 16
atgttggtaa cacctctttt actagtgact cttttgtgtg tactatgtag tgctgctttg      60
tatgacagta gttcttacgt ttactactac caaagtgcct ttagaccacc taatggttgg     120
catttacacg ggggtgctta tgcggtagtt aatatttcta gcgaatctaa taatgcaggc     180
tcttcacctg ggtgtattgt tggtactatt catggtggtc gtgttgttaa tgcttcttct     240
atagctatga cggcaccgtc atcaggtatg gcttggtcta gcagtcagtt ttgtactgca     300
cactgtaact tttcagatac tacagtgttt gttacacatt gttataaata tgatgggtgt     360
cctataactg gcatgcttca aaagaatttt ttacgtgttt ctgctatgaa aaatggccag     420
cttttctata atttaacagt tagtgtagct aagtacccta cttttaaatc atttcagtgt     480
gttaataatt taacatccgt atatttaaat ggtgatcttg tttacacctc taatgagacc     540
acagatgtta catctgcagg tgtttatttt aaagctggtg gacctataac ttataaagtt     600
atgagagaag ttaaagccct ggcttatttt gttaatggta ctgcacaaga tgttattttg     660
tgtgatggat cacctagagg cttgttagca tgccagtata atactggcaa ttttttcagat     720 ggctttttatc cttttattaa tagtagttta gttaagcaga agtttattgt ctatcgtgaa     780
aatagtgtta atactacttt tacgttacac aatttcactt ttcataatga gactggcgcc     840
aaccctaatc ctagtggtgt tcagaatatt ctaacttacc aaacacaaac agctcagagt     900
ggttattata ttttaattt ttcctttctg agtagttttg tttataagga gtctaatttt     960
atgtatggat cttatcaccc aagttgtaat tttagactag aaactattaa taatggcttg    1020
tggtttaatt cactttcagt ttcaattgct acggtcctc ttcaaggtgg ttgcaagcaa    1080 tctgtctttta gtggtagagc aacttgttgt tatgcttatt catatggagg tccttcgctg    1140
tgtaaaggtg tttattcagg tgagttagct cttaattttg aatgtggact gttagtttat    1200
gttactaaga gcggtggctc tcgtatacaa acagccactg aaccgccagt tataactcga    1260
cacaattata taatattac tttaaatact tgtgttgatt ataatatata tggcagaact    1320
ggccaaggtt ttattactaa tgtaaccgac tcagctgtta gttataatta tctagcagac    1380 gcaggttttgg ctatttaga tacatctggt tccatagaca tctttgttgt acaaggtgaa    1440
tatggtctta cttattataa ggttaaccct tgcgaagatg tcaaccagca gtttgtagtt    1500
tctggtggta aattagtagg tattcttact tcacgtaatg agactggttc tcagcttctt    1560
gagaaccagt tttacattaa aatcactaat ggaacacgtc gttttagacg ttaa          1614

<210> SEQ ID NO 17
<211> LENGTH: 39
<212> TYPE: DNA
```

<213> ORGANISM: chicken infectious bronchitis virus

<400> SEQUENCE: 17
ataagaatgc ggccgcatgt ccaacgagac aaattgtac                                    39

<210> SEQ ID NO 18
<211> LENGTH: 38
<212> TYPE: DNA
<213> ORGANISM: chicken infectious bronchitis virus

<400> SEQUENCE: 18
ataagaatgc ggccgcttta ggtgtaaaga ctactccc                                     38

<210> SEQ ID NO 19
<211> LENGTH: 678
<212> TYPE: DNA
<213> ORGANISM: chicken infectious bronchitis virus

<400> SEQUENCE: 19
atgtccaacg agacaaattg tactcttgac tttgaacagt cagttgagct ttttaaagag            60
tataatttat ttataactgc attcttgttg ttcttaacca taatacttca gtatggctat           120
gcaacaagaa gtaagtttat ttatatactg aaaatgatag tgttatggtg cttttggccc           180
cttaacattg cagtaggtgt aatttcatgt atatacccac caaacacagg aggtcttgtc           240
gcagcgataa tacttacagt gtttgcgtgt ctgtcttttg taggttattg gatccagagt           300
attagactct ttaagcggtg taggtcatgg tggtcattta acccagaatc taatgccgta           360
ggttcaatac tcctaactaa tggtcaacaa tgtaattttg ctatagagag tgtgccaatg           420
gtgctttctc caattataaa gaatggtgtt ctttattgtg agggtcagtg gcttgctaag           480
tgtgaaccag accacttgcc taaagatata tttgtttgta caccggatag acgtaatatc           540
taccgtatgg tgcagaaata tactggtgac caaagcggaa ataagaaacg gtttgctacg           600
tttgtctatg caaagcagtc agtagatact ggcgagctag aaagtgtagc aacaggaggg           660
agtagtcttt acacctaa                                                        678

<210> SEQ ID NO 20
<211> LENGTH: 34
<212> TYPE: DNA
<213> ORGANISM: chicken infectious bronchitis virus

<400> SEQUENCE: 20
aaaactgcag tcatggcaag cggtaaggca actg                                        34

<210> SEQ ID NO 21
<211> LENGTH: 33
<212> TYPE: DNA
<213> ORGANISM: chicken infectious bronchitis virus

<400> SEQUENCE: 21
cgcggatcct caaagttcat tctctcctag ggc                                         33

<210> SEQ ID NO 22
<211> LENGTH: 1230
<212> TYPE: DNA
<213> ORGANISM: chicken infectious bronchitis virus

<400> SEQUENCE: 22
atggcaagcg gtaaggcaac tggaaagaca gacgccccag ctccagtcat caaactagga            60
ggaccaaagc cacctaaagt tggttcttct ggaaatgtat cttggtttca agcaataaaa           120

```
gccaagaagt taaattcacc tccgcctaag tttgaaggta gcggtgttcc tgataatgaa      180
aatctaaaac caagtcagca gcatggatat tggagacgcc aagctaggtt taagccaggt      240
aaaggtggaa gaaaccagt cccagatgct tggtattttt actatactgg aacaggacca       300
gccgctaacc tgaattgggg tgatagccaa gatggtatag tgtgggttgc tggtaagggt      360
gctgatacta aatttagatc taatcagggt actcgtgact ctgacaagtt tgaccaatat      420
ccgctacggt tttcagacgg aggacctgat ggtaatttcc gttgggattt cattcctctg      480
aatcgtggca ggagtgggag atcaacagca gcttcatcag cggcatctag tagagcacca      540
tcacgtgaag tttcgcgtgg tcgcaggagt ggttctgaag atgatcttat tgctcgtgca      600
gcaaggataa ttcaggatca gcagaagaag ggttctcgca ttacaaaggc taaggctgat      660
gaaatggctc accgccggta ttgcaagcgc actattccac ctaattataa ggttgatcaa      720
gtgtttggtc cccgtactaa aagtaaggag ggaaattttg gtgatgacaa gatgaatgag      780
gaaggtatta aggatgggcg cgttacagca atgctcaacc tagttcctag cagccatgct      840
tgtcttttcg gaagtagagt gacgcccaga cttcaaccag atgggctgca cttgaaattt      900
gaatttacta ctgtggtccc acgtgatgat ccgcagtttg ataattatgt aaaaatttgt      960
gatcagtgtg ttgatggtgt aggaacacgt ccaacagatg atgaaccaag accaaagtca     1020
cgctcaagtt caaaacctgc aacaagagga aattctccag cgccaagaca gcagcgccct     1080
aagaaggaga aaaagccaaa gaagcaggat gatgaagtgg ataaagcatt gacctcagat     1140
gaggagagga acaatgcaca gctggaattt gatgatgaac ccaaggtaat taactggggg     1200
gattcagccc taggagagaa tgaactttga                                      1230

<210> SEQ ID NO 23
<211> LENGTH: 39
<212> TYPE: DNA
<213> ORGANISM: Chicken anemia virus

<400> SEQUENCE: 23
ttcttgcggc cgccatggca agacgagctc gcagaccga                             39

<210> SEQ ID NO 24
<211> LENGTH: 38
<212> TYPE: DNA
<213> ORGANISM: Chicken anemia virus

<400> SEQUENCE: 24
ttcttgcggc cgctcagggc tgcgtccccc agtacatg                              38

<210> SEQ ID NO 25
<211> LENGTH: 39
<212> TYPE: DNA
<213> ORGANISM: Chicken anemia virus

<400> SEQUENCE: 25
ttcttgcggc cgccatgcac gggaacggcg gacaaccgg                             39

<210> SEQ ID NO 26
<211> LENGTH: 32
<212> TYPE: DNA
<213> ORGANISM: Chicken anemia virus

<400> SEQUENCE: 26
cgcggatcct cacactatac gtaccggggc gg                                    32
```

<210> SEQ ID NO 27
<211> LENGTH: 38
<212> TYPE: DNA
<213> ORGANISM: chicken infectious laryngotracheitis virus

<400> SEQUENCE: 27
ttcttgcggc cgccatggct agcttgaaaa tgctgatc                    38

<210> SEQ ID NO 28
<211> LENGTH: 36
<212> TYPE: DNA
<213> ORGANISM: chicken infectious laryngotracheitis virus

<400> SEQUENCE: 28
ttcttgcggc cgcttattcg tcttcgcttt cttctg                      36

<210> SEQ ID NO 29
<211> LENGTH: 33
<212> TYPE: DNA
<213> ORGANISM: chicken infectious laryngotracheitis virus

<400> SEQUENCE: 29
ccggtcgaca tggaccgcca tttattttttg agg                        33

<210> SEQ ID NO 30
<211> LENGTH: 33
<212> TYPE: DNA
<213> ORGANISM: chicken infectious laryngotracheitis virus

<400> SEQUENCE: 30
ggaagatctt tacgatgctc caaaccagta gcc                         33

<210> SEQ ID NO 31
<211> LENGTH: 54
<212> TYPE: DNA
<213> ORGANISM: avian encephalomyelitis virus

<400> SEQUENCE: 31
tttgatatca tggaagccgt cattaaggca tttctgactg gatacccctgg gaag  54

<210> SEQ ID NO 32
<211> LENGTH: 31
<212> TYPE: DNA
<213> ORGANISM: avian encephalomyelitis virus

<400> SEQUENCE: 32
tttggatcct tatactattc tgctttcagg c                           31

<210> SEQ ID NO 33
<211> LENGTH: 31
<212> TYPE: DNA
<213> ORGANISM: avian encephalomyelitis virus

<400> SEQUENCE: 33
acgcgtcgac atggaagccg tcattaaggt g                           31

<210> SEQ ID NO 34
<211> LENGTH: 32
<212> TYPE: DNA
<213> ORGANISM: avian encephalomyelitis virus

<400> SEQUENCE: 34
tgctctagac tataaatttg tcaagcggag cc                          32

<210> SEQ ID NO 35
<211> LENGTH: 32
<212> TYPE: DNA
<213> ORGANISM: Turkey rhinotracheitis virus

<400> SEQUENCE: 35
aaactgcaga gatggggtca gagctctaca tc                                    32

<210> SEQ ID NO 36
<211> LENGTH: 31
<212> TYPE: DNA
<213> ORGANISM: Turkey rhinotracheitis virus

<400> SEQUENCE: 36
cgaagatctt tattgactag tacagcacca c                                     31

<210> SEQ ID NO 37
<211> LENGTH: 33
<212> TYPE: DNA
<213> ORGANISM: avian plague virus

<400> SEQUENCE: 37
aaactgcagc aatggccatc atttatctaa ttc                                   33

<210> SEQ ID NO 38
<211> LENGTH: 31
<212> TYPE: DNA
<213> ORGANISM: avian plague virus

<400> SEQUENCE: 38
cgaagatctt catatgcaga ttctgcattg c                                     31

<210> SEQ ID NO 39
<211> LENGTH: 31
<212> TYPE: DNA
<213> ORGANISM: avian plague virus

<400> SEQUENCE: 39
aaactgcaga tgaacactca atcctgata c                                      31

<210> SEQ ID NO 40
<211> LENGTH: 31
<212> TYPE: DNA
<213> ORGANISM: avian plague virus

<400> SEQUENCE: 40
tttggatcct tatatacaaa tagtgcaccg c                                     31

<210> SEQ ID NO 41
<211> LENGTH: 32
<212> TYPE: DNA
<213> ORGANISM: Avian influenza virus

<400> SEQUENCE: 41
ccggtcgaca tggcgtctca aggcaccaaa cg                                    32

<210> SEQ ID NO 42
<211> LENGTH: 30
<212> TYPE: DNA
<213> ORGANISM: Avian influenza virus

<400> SEQUENCE: 42

```
cgcggatcct taattgtcat actcctctgc                                        30

<210> SEQ ID NO 43
<211> LENGTH: 35
<212> TYPE: DNA
<213> ORGANISM: avian plague virus

<400> SEQUENCE: 43
cgcgtcgaca tgaatccaaa tcagaaaata ataac                                  35

<210> SEQ ID NO 44
<211> LENGTH: 31
<212> TYPE: DNA
<213> ORGANISM: avian plague virus

<400> SEQUENCE: 44
ggaagatctc tacttgtcaa tggtgaatgg c                                      31
```